United States Patent
Lee

(10) Patent No.: US 9,901,620 B2
(45) Date of Patent: Feb. 27, 2018

(54) TRAIL RECEPTOR AGONISTS FOR TREATMENT OF FIBROTIC DISEASE

(71) Applicant: Theraly Pharmaceuticals, Inc., Elkridge, MD (US)

(72) Inventor: Kang Choon Lee, Seoul (KR)

(73) Assignee: Theraly Pharmaceuticals, Inc., Elkridge, MD (US)

( * ) Notice: Subject to any disclaimer, the term of this patent is extended or adjusted under 35 U.S.C. 154(b) by 0 days.

(21) Appl. No.: 14/690,142

(22) Filed: Apr. 17, 2015

(65) Prior Publication Data

US 2016/0022776 A1 Jan. 28, 2016

Related U.S. Application Data

(63) Continuation-in-part of application No. 14/645,276, filed on Mar. 11, 2015.

(60) Provisional application No. 61/982,207, filed on Apr. 21, 2014, provisional application No. 61/990,530, filed on May 8, 2014.

(51) Int. Cl.
| | | |
|---|---|---|
| *A61K 38/19* | (2006.01) | |
| *A61K 47/48* | (2006.01) | |
| *C07K 16/28* | (2006.01) | |
| *A61K 38/17* | (2006.01) | |
| *A61K 45/06* | (2006.01) | |
| *C07K 14/705* | (2006.01) | |
| *A61K 47/60* | (2017.01) | |

(52) U.S. Cl.
CPC .......... *A61K 38/191* (2013.01); *A61K 38/177* (2013.01); *A61K 45/06* (2013.01); *A61K 47/60* (2017.08); *C07K 14/70578* (2013.01); *C07K 16/2866* (2013.01); *C07K 2319/00* (2013.01); *C07K 2319/73* (2013.01)

(58) Field of Classification Search
None
See application file for complete search history.

(56) References Cited

U.S. PATENT DOCUMENTS

| | | |
|---|---|---|
| 2011/0038855 A1 | 2/2011 | Schoenberger |
| 2012/0021995 A1 | 1/2012 | Bowdish |
| 2013/0101553 A1 | 4/2013 | Kisseleva |

OTHER PUBLICATIONS

Bataller, et al., "Liver fibrosis", Clin. Invest., 115(2):209-18 (2005).
Bataller, et al., "Hepatic stellate cells as target for treatment of liver fibrosis", Semin Liver Dis, 21(03):437-52 (2001).
Beljaars, et al., "Successful targeting to rat hepatic stellate cells using albumin modified with cyclic peptides that recognize the collagen type VI receptor", J Biol Chem., 275:12743-51 (2000).
Beljaars, et al., "Albumin modified with mannose 6-phosphate: A potential carrier for selective delivery of antifibrotic drugs to rat and human hepatic stellate cells", Hepatology, 29:1486-93 (1999).
Benedict, et al., "TRAIL: not just for tumors anymore J. Exp. Med., 209 (11):1903-6 (2012).
Brocchini, et al., "PEGylation of native disulfide bonds in proteins", Nature protocols, 1:2241-52 (2006).
Chae, et al., "Improved antitumor activity and tumor targeting of NH(2)-terminal-specific PEGylated tumor necrosis factor-related apoptosis-inducing ligand.", Molecular cancer therapeutics 9(6):1719-29 (2010).
Cong, et al., "Site-specific PEGylation at histidine tags". Bioconjugate Chemistry, 23(2):248-63 (2012).
Fee, et al., "Size comparison between proteins PEGylated with branched and linear poly(ethylene glycol) molecules", Biotechnol Bioeng., 98(4):725-3 (2007).
Friedman, "Fibrogenic cell reversion underlies fibrosis regression in liver", PNAS, 109(24):9230-1 (2012).
Friedman, "Evolving challenges in hepatic fibrosis", Nat Rev Gastroenterol Hepatol. 7(8):425-36 (2010).
Gong, et al., "Site-specific PEGylation of exenatide analogues markedly improved their glucoregulatory activity", Br J Pharmacol., 163(2):399-412 (2011).
Iredale, et al., "Mechanisms of spontaneous resolution of rat liver fibrosis. Hepatic stellate cell apoptosis and reduced hepatic expression of metalloproteinase inhibitors", J Clin Invest, 102(3):538-49 (1998).
Kim, et al., "Bioimaging for targeted delivery of hyaluronic Acid derivatives to the livers in cirrhotic mice using quantum dots", ACS Nano, 4(6):3005-14 (2010b).
Kim, et al., "PEGylated TNF-related apoptosis-inducing ligand (TRAIL) analogues: Pharmacokinetics and antitumor effects", Bioconjugate chemistry, 22(8):1631-7 (2011a).
Kim, et al., "Ionic complex systems based on hyaluronic acid and PEGylated TNF-related apoptosis-inducing ligand for treatment of rheumatoid arthritis", Biomaterials, 31(34):9057-64 (2010a).

(Continued)

*Primary Examiner* — Vanessa L Ford
*Assistant Examiner* — Jegatheesan Seharaseyon
(74) *Attorney, Agent, or Firm* — Pabst Patent Group LLP

(57) ABSTRACT

Pro-apoptotic agents such as ligands and agonists of agonistic TRAIL receptors can induce or increase apoptosis of cells that cause fibrosis and underlying diseases such as liver, pancreatic, lung and skin diseases characterized by fibrosis, cirrhosis, or complications thereof. The compositions and methods can be used to selectively remove activated hepatic stellate cells (HSCs), the originators of liver fibrosis and cirrhosis, and activated pancreatic stellate cells (PSCs), the originators of pancreas fibrosis and pancreatitis, and can be effective to reduce or prevent further chronic fibrosis by simultaneously reducing multiple fibrosis-associated molecules secreted or induced by such activated stellate cells. The compositions are typically effective to target agonistic TRAIL receptors such as TRAIL-R1/DR4 and TRAIL-R2/DR5 that are selectively expressed in activated HSCs and PSCs in physiological conditions. Ligands and agonists that can be used to target agonistic TRAIL receptors include, but are not limited to, TRAIL-R1/DR4 and/or TRAIL-R2/DR5 agonists.

20 Claims, 4 Drawing Sheets

(56) References Cited

OTHER PUBLICATIONS

Kim, et al., "PEGylatpd TNF-related apoptosis-inducing ligand (TRAIL)-loaded sustained release PLGA microspheres for enhanced stability and antitumor activity", J Control Release, 150(1):63-9 (2011b).

Kim, et al., "Preparation and characterization of Apo2L/TNF-related apoptosis-inducing ligand-loaded human serum albumin nanoparticles with improved stability and tumor distribution", J Pharm Sci., 100(2):482-91 (2011c).

Kim, et al., "A sulfate polysaccharide/TNF-related apoptosis-Inducing ligand (TRAIL) complex for the long-term delivery of TRAIL in poly(lactic-co-glycolic acid) (PLGA) microspheres", J Pharm Pharmacol., 65(1)11-21 (2013).

Lakner, et al., "Inhibitory effects of microRNA 19b in hepatic stellate cell-mediated fibrogenesis", Hepatology, 56(1):300-10 (2012).

Lee, et al., "1004 Treatment with PEGylated TNF-related apoptosis-inducing ligand (TRAIL) induces apoptosis of human rheumatoid arthritis (RA) fibroblast-like synovlocytes (FLS) and suppresses arthritis in murine collagen-induced arthritis", Arthritis and Rheumatism; 72nd Annual scientific meeting of the American college of Rheumatology/43rd annual scientific meeting, Wiley San Francisco, CA, 58(9): Suppl S p. s539, Sep. 1, 2008.

Louis, et al., "Interleukin-10 controls neutrophilic infiltration, hepatocyte proliferation, and liver fibrosis induced by carbon tetrachloride in mic", Hepatology, 28:1607-15 (1998).

Molineux, "The design and development of pegfilgrastim (PEG-rmetHuG-CSF, Neulasta)", Curr Pharm Des., 10(11):1235-44 (2004).

Park, et al., "Down-regulation of Fox0-dependent c-FLIP expression mediates Trail-induced apoptosis in activated hepatic stellate cells", Cell Signal., 21 (10):1495-503 (2009).

Pavet, et al., "Multivalent DR5 peptides activate the TRAIL death pathway and exert tumoricidal activity", Cancer Res., 70:1101-10, (2010).

Poelstra, et al., "Drug targeting to the diseased, liver", J. Control Release, 161 (2):188-97 (2012).

Radaeva, et al., "Natural killer cells ameliorate liver fibrosis by killing activated stellate cells in NKG2D-dependent and tumor necrosis factor-related apoptosis-inducing ligand-dependent manners", Gastroenterology, 130(2):435-52 (2006).

Taimr, "Activated stellate cells express the TRAIL receptor-2/death receptor-5 and undergo TRAIL-mediated apoptosis", Hepathology, 37(1):89-95 (2003).

Tur,et al., "DR4-selective tumor necrosis factor-related apoptosis-inducing ligand (TRAIL) variants obtained by structure-based design", J. Biological Chemistry, 283(29):20560-8 (2008).

van der Sloot, "Designed tumor necrosis factor-related apoptosis-inducing ligand variants initiating apoptosis exclusively via the DR5 receptor", PNAS,103(23):8634-9 (2006).

Wahl, et al., "Increased apoptosis induction in hepatocellular carcinoma by a novel tumor-targeted TRAIL fusion protein combined with bortezomib", Hepatology, 57(2):625-36 (2013).

Yang, et al., "Target specific hyaluronic acid-interferon alpha conjugate for the treatment of hepatitis C virus infection", Biomaterials, 32(33):8722-9 (2011).

Group 1

Group 2

Group 3

SEQUENCE LISTING

<160> NUMBER OF SEQ ID NOS: 5

<210> SEQ ID NO 1
<211> LENGTH: 281
<212> TYPE: PRT
<213> ORGANISM: Homo sapiens

<400> SEQUENCE: 1

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Gly Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 2
<211> LENGTH: 8
<212> TYPE: PRT
<213> ORGANISM: Artificial Sequence
<220> FEATURE:
<223> OTHER INFORMATION: FLAG tag

<400> SEQUENCE: 2

Asp Tyr Lys Asp Asp Asp Asp Lys
1               5

<210> SEQ ID NO 3

```
<211> LENGTH: 6
<212> TYPE: PRT
<213> ORGANISM: Artificial Sequence
<220> FEATURE:
<223> OTHER INFORMATION: Hemagglutinin tag

<400> SEQUENCE: 3

Tyr Pro Tyr Asp Val Pro
1               5

<210> SEQ ID NO 4
<211> LENGTH: 10
<212> TYPE: PRT
<213> ORGANISM: Artificial Sequence
<220> FEATURE:
<223> OTHER INFORMATION: Myc Tag

<400> SEQUENCE: 4

Ile Leu Lys Lys Ala Thr Ala Tyr Ile Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Myc Tag

<400> SEQUENCE: 5

Glu Gln Lys Leu Ile Ser Glu Glu Asp Leu
1               5                   10
```

TRAIL RECEPTOR AGONISTS FOR TREATMENT OF FIBROTIC DISEASE

CROSS REFERENCE TO RELATED APPLICATIONS

This application claims priority to and the benefit of U.S. Provisional Application No. 61/982,207, filed Apr. 21, 2014, U.S. Provisional Application No. 61/990,530, filed May 8, 2014, and is a continuation-in-part of U.S. Utility application Ser. No. 14/645,276, filed Mar. 11, 2015, the disclosures of which are expressly incorporated hereby by reference.

REFERENCE TO SEQUENCE LISTING

This application contains a Sequence Listing which has been submitted in ASCII format via EFS-Web and is hereby incorporated by reference in its entirety. The ASCII copy, created on Apr. 9, 2015, is named THER_100_ST25.txt and is 4,814 bytes in size.

FIELD OF THE INVENTION

The invention is generally directed to compositions and methods for treating fibrotic disease, in particular TRAIL pro-apoptotic agents and methods of use for treating liver fibrosis and cirrhosis as well as its complications and fibrosis of other organs such as pancreas, for example, by simultaneously down-regulating activities of multiple fibrogenic molecules by eliminating originators of fibrogenesis, activated stellate cells.

BACKGROUND OF THE INVENTION

Fibrotic diseases, especially in the lung, liver, pancreas, skin and kidney, account for as much as 45% of deaths in the world (Friedman, S L, et al. Science Translational Medicine, 5(167):167sr1 (2013)). With regard to liver disease, there are no antifibrotic agents for liver fibrosis and cirrhosis available for use in humans. There is a clinical urgency for hepatic fibrosis therapies because of the increasing disease prevalence from viral, obesity-related and alcohol-related fibrosis and cirrhosis as well as the shortfall in liver donations for transplants. In 1985, hepatic stellate cells (HSC) were identified as the main culprit in developing liver fibrosis by overexpressing extracellular matrix components (Friedman S L, et al., PNAS, 82(24):8681-5 (1985)). Pancreatic stellate cells (PSCs) are myofibroblast-like cells that play a pivotal role in the development of pancreatic fibrosis, pancreatitis and pancreatic cancer (Omary. M. B., et al., J. Clin. Invest. 117(1):50-59 (2007)). In response to pancreatic injury or inflammation, quiescent PSCs are activated to myofibroblast-like cells and express a-smooth muscle actin, very similar to HSCs.

Existing treatments for liver fibrosis have several short comings. Some treatments affect HSCs. A number of hepatoprotectants that attenuate or neutralize upstream inflammatory responses, and thus HSC activation, have been studied in vitro and in vivo. Vitamin E was evaluated in clinical trials in nonalcoholic steatohepatitis (NASH) and demonstrated that histological liver injury was attenuated although no antifibrotic effect was demonstrated (Sanyal, A J., et al., New Eng, J. Med.e, 362(18):1675-85 (2010)).

Hepatocyte growth factor (HGF) is reported to modulate HSC proliferation, collagen synthesis, and TFG-β expression. Delivery of HGF by gene therapy or injecting a recombinant protein prevented the progression of experimental liver fibrosis. However, there are concerns of using HGF or HGF mimetics that would stimulate hepatocyte growth and increase the potential risk of oncogenesis (Fallowfield, J A., American Journal of Physiology-Gastrointestinal and Liver Physiology, 300(5):G709-G15 (2011)).

Agents that would prevent HSC activation or proliferation have also been investigated. HSC activation is associated with low-level of PPAR-r expression. Upregulation of PPAR-r or addition of PPAR-r ligands reverse the HSC activation. A few PPAR-r ligands, glitazones, have been tested in animal models but only marginally slowed fibrosis progression early in the disease course (Leclercq, I A, et al., Gut, 55(7):1020-9 (2006)).

Statins, HMG-CoA reductase inhibitors, are also known to inhibit HSC proliferation in vitro and provided beneficial effects on portal hypertension and on angiostensin II-induced inflammation in liver fibrosis models. For example, early atorvastatin treatment attenuated HSC activation and collagen deposition after bile duct ligation in rats; however, atorvastatin was not effective when the treatment was initiated once fibrosis was established (Trebicka, J., et al., Journal of Hepatology, 53(4):702-12 (2010)), indicating it was useful only as a preventative, not a therapeutic.

The renin-angiotensin system plays important roles in liver fibrogenesis and portal hypertension. Studies indicate that angiotensin-converting enzyme inhibitors and ATIR antagonists, sartans, could reduce fibrosis (Yang, L., et al., Journal of Hepatology, 43(2):317-23 (2005)). Treating patients with chronic hepatitis C virus (HCV) with the AT1R antagonist losartan slowed fibrosis progression and profibrogenic genes (Colmenero, J., et al., American Journal of Physiology Gastrointestinal and Liver Physiology, 297(4): G726-34 (2009)).

TGF-β is the key effector in the pathogenesis of liver fibrosis. Reducing or inhibiting TGF-β synthesis and signaling have been thought to be an important therapeutic target. Diverse strategies to inhibit TGF-β effects include using TFG-β neutralizing antibodies, decoy receptors, siRNA and oligonucleotides. A few TGF-β related molecules showed antifibrotic effects in animal models, however, it would be difficult to target HSC because TGF-β receptors are widely expressed on all cell types and such inhibitors could trigger autoimmune diseases or cellular dedifferentiation.

Chronic pancreatitis (CP) is a disease characterized by progressive and irreversible destruction of pancreas structure and function (Braganza, J. M., et al., Lancet, 377(9772): 1184-97 (2011)). CP is accompanied by pancreatic fibrosis and constant abdominal pain. The management of CP and CP-associated pain is challenging since CP is currently an incurable condition. No agents have emerged in humans, resulting in a significantly undeserved CP patient population. CP is recognized by significant fibrosis. Pancreatic fibrogenesis is mainly orchestrated by PSCs. During pancreatic damage or disease, quiescent PSCs undergo activation and transform to proliferative, fibrogenic and contractile myofibroblasts that facilitate collagen deposition and lead to fibrotic tissue. Therefore, activated PSCs are a major target for antifibrotic and anti-pain therapies targeting the pancreas (Omary, M. B., et al., J. Clin. Invest. 117(1):50-59 (2007)). However, like HSCs, the lack of methods to specifically target and affect activated PSCs in vivo hampers this strategy.

During fibrogenesis and upon activation of HSCs or PSCs, many fibrosis-associated molecules are highly upregulated and contribute to the development of fibrosis and its complications. These molecules include, but are not limited to, PDGF, TGFβ, CTGF, MMPs, TIMPs and collagens (Friedman, S. L., Nat Rev Gastroenterol Hepatol. 7(8):425-36 (2010)). A common antifibrotic strategy is inhibiting the regulation of one of many fibrosis-associated molecules in vivo. Inhibition of one fibrosis-associated molecule would provide some anti-fibrosis efficacy; however, since fibrogenesis is a complicated process associated with multiple pathways that are involved with many fibrogenic molecules, such methods would not be highly efficient to stop or reverse fibrosis. Simultaneous inhibition or down-regulation of multiple fibrosis-associated molecules will demonstrate strong anti-fibrotic efficacy, however, it is difficult to target multiple molecules simultaneously in physiological conditions particularly by utilizing a single drug molecule.

Therefore, it is an object of the invention to provide compositions and methods for treating fibrotic disease, including liver fibrosis and pancreatic fibrosis.

It is another object of the invention to provide compositions and methods for simultaneously inhibiting or down-regulating multiple fibrosis-associated molecules in physiological conditions.

It is another object of the invention to provide compositions and methods for reducing, inhibiting, or reversing liver fibrosis and other diseases such as cirrhosis and its complications.

It is still another object of the invention to provide methods and compositions for reducing or inhibiting liver inflammation.

Another object of the invention is a method for treating fibrosis of other organs and its related complications, for example, pancreatic fibrosis, chronic pancreatitis, and its complications, such as pain.

SUMMARY OF THE INVENTION

It has been discovered that pro-apoptotic agents such as ligands and agonists of agonistic TRAIL receptors can induce or increase apoptosis of cells that cause fibrosis and underlying diseases such as liver, pancreatic, lung and skin diseases characterized by fibrosis, cirrhosis, or complications thereof. The compositions and methods disclosed herein can be used to selectively remove activated hepatic stellate cells (HSCs), the originators of liver fibrosis and cirrhosis, and activated pancreatic stellate cells (PSCs), the originators of pancreas fibrosis and pancreatitis, and can be effective to simultaneously reduce regulations of multiple fibrosis-associated molecules induced by activated stellate cells. This will overall reduce or reverse fibrosis or prevent further fibrosis-related complications. The compositions are typically effective to target agonistic TRAIL receptors such as TRAIL-R1/DR4 and TRAIL-R2/DR5 that are selectively expressed in activated HSCs and PSCs in physiological conditions. Ligands and agonists that can be used to target agonistic TRAIL receptors include, but are not limited to, TRAIL-R1 and/or TRAIL-R2 agonists such as recombinant human (rh) TRAIL, engineered TRAIL analogs, long-acting TRAIL proteins modified, for example, with polymers such as poly(ethylene glycol), copolymers and branched analogs, and biopolymers such as hyaluronic acid. TRAIL-based long-acting formulations include polymeric systems; TRAIL fusion proteins, agonistic anti-TRAIL-R1 antibodies; agonistic anti-TRAIL-R2 antibodies; and agonistic small molecules or peptidic molecules binding TRAIL-R1 and/or R2. These agonists alone or in combination with other therapeutic agents can reduce or block development of, or may reverse, existing fibrosis in various organs. An exemplary method for treating fibrotic disease includes administering to a subject in need thereof an effective amount of a pro-apoptotic agent to induce apoptosis in hepatic stellate cells, pancreatic stellate cells, fibromyoblasts, fibromyoblastic cells, activated endothelial cells or activated epithelial cells that produce or induce an excess amount of extracellular matrix resulting in unwanted scarring of the liver, pancreas or other organs. The pro-apoptotic agent can be a TNF-related apoptosis-inducing ligand (TRAIL) agonist, for example, PEGylated TRAIL or agonistic TRAIL antibodies. Such antibodies are in clinical trials in cancer patients but have not shown much success. The TRAIL can be, for example, a native or genetically engineered (recombinant) form of the protein. In preferred embodiments, the TRAIL is human TRAIL, or a functional fragment or variant thereof. For example, the functional fragment can be a fragment of a 281 amino acid human TRAIL. In preferred embodiments, the fragment has an amino acid sequence from 114 to 281 or from 95 to 281 of the full-length 281 amino acid human form (1-281).

In some embodiments, the PEGylated TRAIL includes a trimeric TRAIL including a zipper amino acid motif, more preferably an isoleucine zipper motif, favoring trimer formation at the N-terminals thereof and a PEG or a derivative thereof, wherein the PEG is bound to the N-terminal of at least one monomer of the trimeric TRAIL. The PEG or the derivative thereof can be a linear, branched or trimeric form of PEG. Exemplary derivatives of PEG include methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol. In some embodiments, the PEG or the derivative thereof has a molecular weight between 1,000 and 100,000 Da, preferably between 5,000 and 50,000 Da.

A key aspect of this technology is to simultaneously target multiple fibrosis-associated molecules by specifically eliminating an originator cell of fibrosis, such as activated Hepatic Stellate Cells and Pancreatic Stellate Cells in physiological conditions. This provides a means for treating pathological conditions that induce an excess amount of extracellular matrix resulting in unwanted scarring. Representative conditions include liver fibrosis and cirrhosis as well as chronic pancreatitis and fibrosis of other organs such as lungs, skin, heart, and kidneys. This also reduces the amount of ascites, a major complication of cirrhosis, and pain, a major complication of chronic pancreatitis.

DETAILED DESCRIPTION OF THE INVENTION

I. Definitions

Figure 1:
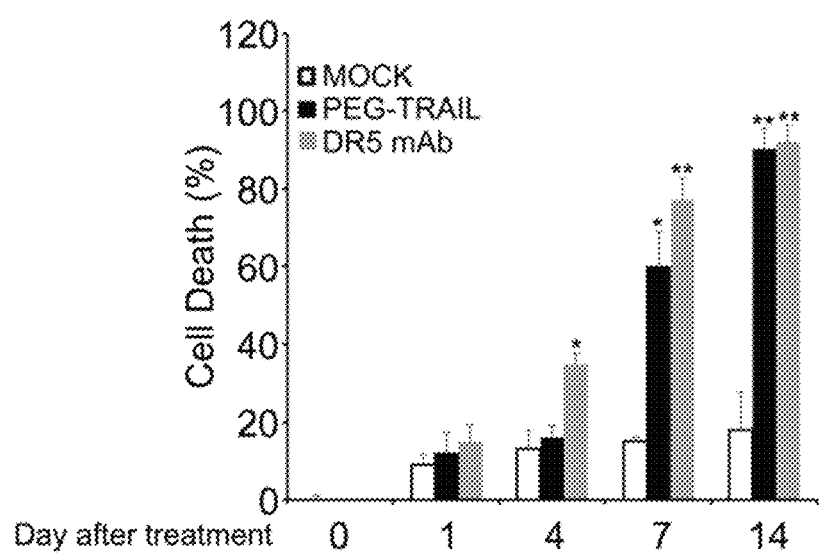
FIG. 1 is a bar graph showing TRAIL agonists, PEG-TRIAL and agonistic TRAIL antibody, induce apoptosis of originator cells of fibrogenesis-activated human primary hepatic stellate cells (HSCs). Highly activated HSCs (at day 7 and 14) are more sensitive to TRAIL-induced apoptosis. Apoptosis was expressed as the induced cell death (%), calculated as the percentage relative to the untreated cells and measured by cell death assays. *$P<0.05$ vs. at day 1, **$P<0.01$ vs. at day 1.

As used herein, the term "treating" includes inhibiting, alleviating, preventing or eliminating one or more symptoms or side effects associated with the disease, condition, or disorder being treated.

The term "reduce", "inhibit", "alleviate" or "decrease" are used relative to a control. One of skill in the art would readily identify the appropriate control to use for each experiment. For example a decreased response in a subject or cell treated with a compound is compared to a response in subject or cell that is not treated with the compound.

As used herein the term "effective amount" or "therapeutically effective amount" means a dosage sufficient to treat, inhibit, or alleviate one or more symptoms of a disease state being treated or to otherwise provide a desired pharmacologic and/or physiological effect. The precise dosage will vary according to a variety of factors such as subject-dependent variables (e.g., age, immune system health, etc.), the disease or disorder, and the treatment being administered. The effect of the effective amount can be relative to a control. Such controls are known in the art and discussed herein, and can be, for example, the condition of the subject prior to or in the absence of administration of the drug, or drug combination, or in the case of drug combinations, the effect of the combination can be compared to the effect of administration of only one of the drugs.

As used herein, the term "combination therapy" refers to treatment of a disease or symptom thereof, or a method for achieving a desired physiological change, including administering an effective amount of two or more chemical agents or components to treat the disease or symptom thereof, or to produce the physiological change, wherein the chemical agents or components are administered together, such as part of the same composition, or administered separately and independently at the same time or at different times (i.e., administration of each agent or component is separated by a finite period of time from each other).

As used herein, the term "dosage regime" refers to drug administration regarding formulation, route of administration, drug dose, dosing interval and treatment duration.

As used herein, the term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (0.4); threonine (−0.7); serine (−0.8); tryptophan (−0.9); tyrosine (−1.3); proline (1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, and antigens. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (1.0); methionine (−1.3); valine (−1.5); leucine (−1.8); isoleucine (−1.8); tyrosine (2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg). (Met: Leu, Tyr), (Ser: Thr), (Thr: Ser), (Tip: Tyr), (Tyr: Trp, Phe), and (Val: Ile, Leu). In particular, embodiments of the polypeptides can include variants having about 50%, 60%. 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in (Computational Molecular Biology, Lesk. A. M., Ed., Oxford University Press, New York, 1988; Biocomputing: Informatics and Genome Projects, Smith, D. W., Ed., Academic Press, New York, 1993: Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991: and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will assist the linked protein to be localized at the specific organelle.

As used herein, the term "cell type" is a manner of grouping or classifying cells in the art. The term cell type refers to the grouping of cells based on their biological character determined in part through common biological function, location, morphology, structure, expression of polypeptides, nucleotides or metabolites.

As used herein, the term "cell state" refers to the condition of a cell type. Cells are dynamic throughout their life and can achieve various states of differentiation, function, morphology and structure. As used herein, cell state refers to a specific cell type throughout its lifetime.

As used herein, the term "cell surface marker" refers to any molecule such as moiety, peptide, protein, carbohydrate, nucleic acid, antibody, antigen, and/or metabolite presented on the surface or in the vicinity of a cell sufficient to identify the cell as unique in either type or state.

II. Compositions for Treating Liver and Pancreatic Disease Ligands and Agonists of Agonistic TRAIL Receptors It has been discovered that the ligands and agonists of agonistic TRAIL receptors can be formulated such that the ligand is effective for treating fibrosis and/or fibrosis-associated complications.

In preferred embodiments, the ligand or agonist does not require a delivery vehicle such as a particle or matrix to be effective. For example, although formulations including particles and other delivery vehicles are provided, in some embodiments, the ligand is stable in circulation and effective for at least one day, preferably at least two days, without the aid of a time release matrix, particle, or other time-release or degradable carrier.

The ligands and agonists are typically TRAIL conjugates that include a TRAIL peptide, mimic, or mimic, preferably TRAIL or a fragment, variant, or fusion thereof, linked to a conjugate molecule that extends the in vivo half-life of the TRAIL-conjugate when compared to the TRAIL fragment, variant, or fusion in the absence of the conjugate molecule.

The TRAIL-conjugate formulations and dosage regimes can target and eliminate originators of fibrosis-inducing activated hepatic stellate cells (HSCs) and pancreatic stellate cells (PSCs) that contribute to fibrogenesis, and not quiescent stellate cells. By eliminating such originating cells, multiple fibrosis-associated molecules secreted or induced by stellate cell activation can be simultaneously inhibited or down-regulated. For example, systemic PEG-TRAIL administrations removed the population of activated HSCs or PSCs, and reduced and/or normalized the highly upregulated fibrogenic molecules at protein and mRNA levels including α-SMA, collagen 1, collagen 3, PDGFR, TGFβ, MMP-2, MMP-3, TIMP-1, TIMP-3, BMP-7. As discussed in more detail below, the disclosed compositions are typically administered to a subject in need thereof in amount effective to target and eliminate originating cells of fibrosis and to simultaneously reduce one or more fibrosis-associated molecules.

A. TRAIL Peptides and Analogues

TRAIL-conjugates include a TRAIL domain, which is typically a TRAIL peptide, analogue, or mimic, preferably TRAIL or a fragment, variant, or fusion thereof to which a conjugate molecule is linked.

TRAIL

TRAIL/Apo2L (TNFSF10) was originally identified in searches of EST databases for genes with homology to known TNF superfamily ligands (Benedict et al., *J. Exp. Med.*, 209(11): 1903-1906 (2012)). In humans, TRAIL binds two proapoptotic death receptors (DRs), TRAIL-R1 and -R2 (TNFRSF10A and 10B), as well as two other membrane receptors that do not induce death and instead may act as decoys for death signaling. TRAIL binding to its cognate DRs induces formation of a death-inducing signaling complex, ultimately leading to caspase activation and initiation of apoptosis (Benedict et al., *J. Exp. Med.*, 209(11): 1903-1906 (2012)).

In some embodiments, the TRAIL conjugate includes a TRAIL peptide, or an agonistic TRAIL receptor binding fragment or variant thereof.

Nucleic acid and amino acid sequence for human TRAIL are known in the art. For example, an amino acid sequence for human TRAIL is MAMMEVQGGPSLGQTCVLIVIFT-VLLQSLCVAVTYVYFTNELKQMQDK YSKS-GIACFLKEDDSYWDPNDEESMNSPCWQVKWQL-RQLVRKMILRTS EETISTVQEKQQNISPLVRERGPQRVAAHITG-TRGRSNTLSSPNSKNEKA LGRKINSWESSRSGHSFL-SNLHLRNGELVIHEKGFYYIYSQTYFRFQEEIK ENTKNDKQMVQYIYKYTSYPDPILLMKSARN-SCWSKDAEYGLYSIYQG GIFELKENDRIFVSVTNE-HLIDMDHEASFFGAFLVG (SEQ ID NO:1, (UniProtKB database accession no. P50591 (TNF10_HUMAN)). In some embodiments, the TRAIL conjugate includes a TRAIL peptide including or having the amino acid sequence of SEQ ID NO: 1.

Preferably, the TRAIL is a soluble TRAIL. Endogenous, full-length TRAIL includes a cytoplasmic domain, a transmembrane domain, and an extracellular domain. Typically, soluble TRAIL is a fragment of full-length TRAIL without the cytoplasmic domain and the transmembrane domain. Therefore, soluble TRAIL can be the extracellular domain of TRAIL (e.g., extracellular domain of SEQ ID NO: 1), or a functional fragment thereof. A consensus extracellular domain for the TRAIL of SEQ ID NO: 1 is amino acids 39-281 of SEQ ID NO:1. Therefore, in some embodiments, the TRAIL conjugate includes a TRAIL peptide including or having amino acids 39-281, 41-281, 91-281, 92-281, 95-281, and 114-281 of SEQ ID NO:1, or a functional fragment or variant thereof.

In some embodiments, the TRAIL conjugate includes a functional fragment or variant of SEQ ID NO: 1 that can agonize signaling through TRAIL-R1 and/or TRAIL-R2. The fragment or variant of SEQ ID NO: 1 can have 50, 60, 70, 75, 80, 85, 90, 95, 96, 97, 98, 99, or more than 99% sequence identity to SEQ ID NO:1.

Preferably, the functional fragment or variant thereof includes the extracellular domain of SEQ ID NO: 1, or a functional fragment thereof. It is believed that the C-terminal 150 amino acid of TRAIL includes the receptor binding domain. Therefore, in some embodiments, the functional fragment includes amino acids 132-281 of SEQ ID NO:1. In other particular embodiments, the fragment is amino acids 95-281, or amino acids 114-281 of SEQ ID NO:1.

Variants can have one or more substitutions, deletions, or additions, or any combination thereof relative to SEQ ID NO: 1. In some embodiments, the variant is a naturally occurring alternative sequence, splice variant, or substitution, addition or deletion variant, or the extracellular domain or function fragment thereof or an alternative sequence, splice variant, or substitution, addition or deletion variant. Naturally occurring alternative sequences and variants are disclosed in UniProtKB database accession no. P50591 (TNF10_HUMAN), version 140 (last modified Jan. 22, 2014).

TRAIL Analogues

TRAIL can interact with its receptors as a trimer. Therefore, in some embodiments, the ligand or agonist used in the methods disclosed herein is, or can form, a multimer, preferably a trimer. The trimer can be a homotrimer, or a heterotrimer.

All of the TRAIL proteins described herein can be made using standard techniques for isolation of natural or recombinant proteins, and chemically modified as described herein.

The TRAIL conjugate can include a TRAIL analogue, or an agonistic TRAIL receptor binding fragment or variant thereof. TRAIL analogues are known in the art. In preferred embodiments, the analogues have increased affinity or specificity for one or more agonistic TRAIL receptors (e.g., TRAIL-R1 (DR4) and/or TRAIL-R2 (DR5)), reduced affinity or specificity for one or more antagonistic or decoy TRAIL receptors (e.g., receptors DcR1 and DcR2) or a combination thereof compared to wild-type or endogenous TRAIL.

In some embodiments, the analogue is a DR4-selective mutant of wild-type TRAIL. DR-4 selective mutants are known in the art and disclosed in, for example, Tur, *J. Biological Chemistry*. 283(29):20560-8 (2008). In a particular embodiments, the analogue is a variant of SEQ ID NO: 1 having a D218H or a D218Y substitution, or a functional fragment thereof (e.g., the extracellular domain).

In some embodiments, the analogue is a DR5-selective mutant of wildtype TRAIL. Particular DR-5-selective mutants include variants of SEQ ID NO: 1 having D269H, D269H/E 95R, or D269H/T214R, and functional fragments thereof (e.g., the extracellular domain). Such variants are described in van der Sloot, *Proc. Nat. Acad. Sci. USA* 103(23):8634-9 (2006).

TRAIL Fusion Proteins

The TRAIL conjugate can be a TRAIL fusion protein. TRAIL fusion polypeptides have a first fusion partner including all or a part of a TRAIL protein extracellular domain fused (i) directly to a second polypeptide or, (ii)

optionally, fused to a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of the other domains (TRAIL polypeptide or second polypeptide) of the fusion protein. Similarly, the domain that functions to dimerize or multimerize the fusion proteins can either be a separate domain, or alternatively can be contained within one of the other domains (TRAIL polypeptide, second polypeptide or peptide/polypeptide linker domain) of the fusion protein. In one embodiment, the dimerization/multimerization domain and the peptide/polypeptide linker domain are the same.

Fusion proteins disclosed herein can be of formula I:

N—R1-R2-R3-C wherein "N" represents the N-terminus of the fusion protein, "C" represents the C-terminus of the fusion protein. "R1" is a TRAIL polypeptide, "R2" is an optional peptide/polypeptide linker domain, and "R3" is a second polypeptide. Alternatively, R3 may be the TRAIL polypeptide and R1 may be the second polypeptide.

The fusion proteins can be dimerized or multimerized. Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

The presence of the second polypeptide can alter the solubility, stability, affinity and/or valency of the TRAIL fusion polypeptide. As used herein, "valency" refers to the number of binding sites available per molecule. In some embodiments, the second polypeptide contains one or more domains of an immunoglobulin heavy chain constant region, preferably having an amino acid sequence corresponding to the hinge, CH2 and CH3 regions of a human immunoglobulin Cγ1 chain or to the hinge, CH2 and CH3 regions of a murine immunoglobulin Cγ2a chain. In a particular dimeric fusion protein, the dimer results from the covalent bonding of Cys residue in the hinge region of two of the Ig heavy chains that are the same Cys residues that are disulfide linked in dimerized normal Ig heavy chains.

In a particular embodiment, the TRAIL fusion protein is a TRAIL-mimic including three TRAIL-protomer subsequences combined in one polypeptide chain, termed the single-chain TRAIL-receptor-binding domain (scTRAIL-RBD), as described in Gieffers, *Molecular Cancer Therapeutics*, 12(12):273547 (2013). Two of the so-called scTRAIL-RBDs, with three receptor binding sites each, can be brought in close proximity resulting in a multimeric fusion protein with a hexavalent binding mode. In some embodiments, multimerization is achieved by fusing the Fc-part of a human immunoglobulin G1 (IgG1)-mutein C-terminally to the scTRAIL-RBD polypeptide, thereby creating six receptor binding sites per drug molecule.

Forcing dimerization of scFv-scTRAIL based on scFv linker modification for a targeted scTRAIL composed predominantly of dimers (Db-scTRAIL) exceed the activity of nontargeted scTRAIL approximately 100-fold for some target cell types (Siegemund, supra). Increased activity of Db-scTRAIL was also demonstrated on target-negative cells, indicating that, in addition to targeting, oligomerization equivalent to an at least dimeric assembly of standard TRAIL per se enhances apoptosis signaling. Therefore, in preferred embodiments, the TRAIL fusion proteins have a multimerization domain, such as a dimerization or trimerization domain, or a combination thereof that can lead to, for example, dimeric, trimeric, or hexameric molecule.

Another fusion protein that facilitates trimer formation includes a receptor binding fragment of TRAIL amino-terminally fused to a trimerizing leucine or isoleucine zipper domain.

TRAIL fusion proteins and results of using the fusion proteins in functional assays are also described in, Wahl, *Hepatology*, 57(2):625-36 (2013).

Methods for Producing Polypeptides

The disclosed TRAIL polypeptides, fragments, variants and fusions thereof can be manufactured using conventional techniques that are known in the art. Isolated polypeptides can be obtained by, for example, chemical synthesis or by recombinant production in a host cell. To recombinantly produce a polypeptide, a nucleic acid containing a nucleotide sequence encoding the fusion protein can be used to transform, transduce, or transfect a bacterial or eukaryotic host cell (e.g., an insect, yeast, or mammalian cell). In general, nucleic acid constructs include a regulatory sequence operably linked to a nucleotide sequence encoding the polypeptides. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express polypeptides. Viral based expression systems are well known in the art and include, but are not limited to, baculoviral, SV40, retroviral, or vaccinia based viral vectors.

Mammalian cell lines that stably express polypeptides can be produced using expression vectors with appropriate control elements and a selectable marker. For example, the eukaryotic expression vectors pCR3.1 (Invitrogen Life Technologies) and p91023 (B) (see Wong et al. (1985) *Science* 228:810815) are suitable for expression of variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, a fusion protein can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Polypeptides can be isolated using, for example, chromatographic methods such as affinity chromatography, ion exchange chromatography, hydrophobic interaction chromatography, DEAE ion exchange, gel filtration, and hydroxylapatite chromatography. In some embodiments, polypeptides can be engineered to contain an additional domain containing amino acid sequence that allows the polypeptides to be captured onto an affinity matrix. For example, an Fc-fusion polypeptide in a cell culture supernatant or a cytoplasmic extract can be isolated using a protein A colunm. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides. Polypeptides can additionally be engineered to contain a secretory signal (if there is not a secretory signal already present) that causes the polypeptide to be secreted by the cells in which it is produced. The secreted polypeptides can then conveniently be isolated from the cell media.

B. Antibody Composition and Methods of Manufacture

Purified TRAIL receptor polypeptides, fragments, fusions, or antigens or epitopes thereof can be used to prepare an antibody that specifically binds to a TRAIL receptor. Antibodies can be prepared using any suitable methods known in the art. Subsequently, the antibodies can be screened for functional activity (e.g., agonistic or antagonistic activity) using methods known in the art.

Antibodies can be generated in cell culture, in phage, or in various animals. In one embodiment, an antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition).

The disclosed antibodies can be modified by recombinant means to increase greater efficacy of the antibody in mediating the desired function. Antibodies can be modified by substitutions using recombinant means. Typically, the substitutions will be conservative substitutions. For example, at least one amino acid in the constant region of the antibody can be replaced with a different residue. See, e.g., U.S. Pat. No. 5,624,821, U.S. Pat. No. 6,194,551, WO 9958572; and Angal, et al., Mol. Immunol. 30:105-08 (1993). The modification in amino acids includes deletions, additions, substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to TRAIL receptors. See e.g., *Antibody Engineering: A Practical Approach* (Oxford University Press, 1996).

Suitable antibodies with the desired biologic activities can be identified by in vitro assays including but not limited to: proliferation, migration, adhesion, soft agar growth, angiogenesis, cell-cell communication, apoptosis, transport, signal transduction, and the following in vivo assays such as the inhibition of tumor growth.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

Human and Humanized Antibodies

Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge. Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from nonhuman immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fe), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies are preferably prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

Single-Chain Antibodies

Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

Hybrid Antibodies

The antibodies can be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., a bivalent antibody has the ability to bind at least two different epitopes simultaneously. Such hybrids can be formed by fusion of hybridomas producing the respective component antibodies, or by recombinant techniques. Such hybrids may, of course, also be formed using chimeric chains.

Method of Making Antibodies Using Protein Chemistry

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems. Inc., Foster City, Calif.). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or anitgen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

C. Conjugates and Complexes

The disclosed TRAIL-conjugates also include a second conjugate molecule that is linked to the TRAIL domain or to the antibody portion not binding the TRAIL receptor.

Polyalkylene Oxides Such as PEG

The use of hydrophilic polymers such as polyalkylene oxides, or copolymers thereof such as the PLURONIC®s sold by BASF can be covalently bound to the molecules to improve the pharmacokinetic and pharmacodynamic profiles of TRAIL (Kim, et al., *Bioconjugate Chem.*, 22 (8), pp 1631-1637 (2011)). Studies show that TRAIL analogues derivatized with PEG maintain anti-cancer activity, while also exhibiting higher metabolic stabilities in plasma, extended pharmacokinetic profiles, and greater circulating half-lives (Chae, et al., *Molecular cancer therapeutics* 9(6): 1719-29 (2010); Kim, et al., *Bioconjugate chemistry,* 22(8): 1631-7 (2011); Kim, et al., *Journal of pharmaceutical sciences* 100(2):482-91 (2011); Kim, et al., *Journal of controlled release: official journal of the Controlled Release Society* 150(1):639 (2011)).

Therefore, in some embodiments, the TRAIL domain is derivatized with one or more ethylene glycol (EG) units, more preferably 2 or more EG units (i.e., polyethylene glycol (PEG)), or a derivative thereof. Derivatives of PEG include, but are not limited to, methoxypolyethylene glycol succinimidyl propionate, methoxypolyethylenc glycol N-hydroxysuccinimide, methoxypolyethylene glycol aldehyde, methoxypolyethylene glycol maleimide and multiple-branched polyethylene glycol.

The precise number of EG or derivative units depends on the desired activity, plasma stability, and pharmacokinetic profile. For example, Kim, et al. (supra) reported that 2, 5, 10, 20, and 30K-PEG-TRAIL resulted in greater circulating half-lives of 3.9, 5.3, 6.2, 12.3, and 17.7 h respectively in mice, versus 1.1 h for TRAIL. In some embodiments, the molecular weight of the PEG is between about 1 and 100 kDa, preferably between about 1 and 50 kDa. For example, the PEG can have a molecular weight of "N" kDa, wherein N is any integer between 1 and 100. The PEG can have a molecular weight of "N" Da, wherein N is any integer between 1,000 and 1,000,000. In a particular embodiment, the molecular weight of the PEG is "N" Da, wherein "N" is between 1,000 and 50,000, or more preferably between 5,000 and 50,000.

The pro-apoptotic agent can be conjugated with linear or branched PEG. Some studies have shown that proteins derivatized with branched PEG have extended in vivo circulation half-lives compared to linear PEG-proteins, thought to be due partly to a greater hydrodynamic volume of branched PEG-proteins Fee, et al., *Biotechnol Bioeng.*, 98(4):725-3 (2007).

Peptide ligands can be derivatized at the C-terminus, or preferably at the N-terminus, using methods that are known in the art.

The TRAIL-PEG conjugates may be depicted by the following formula:

$$X\text{-}L\text{-}(PEG)_n,$$

wherein

X represents a TRAIL protein,

L represents a linker,

PEG represents a branched poly(ethylene glycol) chain, and n is an integer selected from 2, 3, 4, 5, 6, 7 or 8.

In certain embodiments, n is 2.

The polyalkylene oxide is coupled to the protein via a linker. The linker may be a polyakylene oxide, and preferably connects two polyalkylene oxide polymers to the protein.

In a particular embodiment, the TRAIL-conjugate is a PEG-conjugate that includes a TRAIL domain including a truncated form of human TRAIL, for example, from arginine-114 to glycine-281 of the full-length form (1-281) of human TRAIL, and PEG having a molecular weight between 1,000 and 100,000 Daltons, and preferably between 5,000 and 50,000 Daltons.

N-terminal modified PEG-TRAIL conjugates can be obtained by reacting an N-terminal amine of the TRAIL domain with an aldehyde group of the PEG in the presence of a reducing agent. PEG and TRAIL can be reacted at a molar ratio (PEG/TRAIL) of 2 to 10, or preferably 5 to 7.5.

In preferred embodiments, the TRAIL-conjugate includes a zipper amino acid motif, for example, an isoleucine zipper motif, that allows for trimer formation between three TRAIL-conjugate monomers.

The PEG chains are preferably, but not necessarily, of equal molecular weight. Exemplary molecular weight ranges for each PEG chain is between about 10 kDa and 60 kDa, and preferably about 20 kDa and 40 kDa. PEG40 is a branched PEG moiety was synthesized and has a molecular weight of 40 kDa: 20+20 kDa (each PEG chain).

A trimeric PEG moiety can consist of a branched PEG chain attached to a linker arm. A visual description of the trimer PEG moiety is provided immediately below.

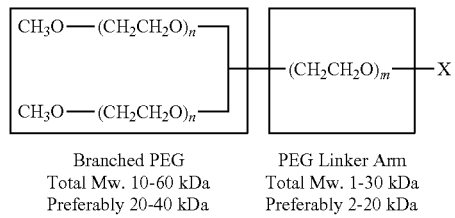

Branched PEG
Total Mw. 10-60 kDa
Preferably 20-40 kDa

PEG Linker Arm
Total Mw. 1-30 kDa
Preferably 2-20 kDa

The following trimeric PEGs were synthesized: YPEG42, YPEG43.5, YPEG45, YPEG50 and YPEG60.

YPEG42 is a trimeric PEG moiety which has a molecular weight of 42 kDa: (20+20 kDa) (branched PEG)+2 kDa (linker arm).

YPEG43.5 is a trimeric PEG moiety which has a molecular weight of 43.5 kDa: (20+20 kDa) (branched PEG)+ 3.5 kDa (linker arm).

YPEG45 is a trimeric PEG moiety which has a molecular weight of 45 kDa: (20+20 kDa) (branched PEG)+5 kDa (linker arm).

YPEG50 is a trimeric PEG moiety which has a molecular weight of 50 kDa: (20+20 kDa) (branched PEG)+10 kDa (linker arm).

YPEG60 is a trimeric PEG moiety which has a molecular weight of 60 kDa: (20+20 kDa) (branched PEG)+20 kDa (linker arm).

Linker Moiety

The protein or peptide is covalently joined to the branched PEG moiety via a linker. The linker is a polymer, and generally has an atomic length of at least 800 angstroms. Typically, the linker has an atomic length from about 800 to about 2,000 angstrom, from about 800 to about 1,500 angstrom, from about 800 to about 1,000 angstrom, or from about 900 to about 1,000 angstrom. It is to be appreciated that the atomic distances listed above refer to fully extended polymers, and that when in the solid state or solution the linker may fold or curl in ways such that the actual distance between the branched PEG and protein or peptide is less than the atomic lengths listed above.

In certain embodiments, the linker is a poly(ethylene glycol) derivative with a molecular weight between about 1 kDa to 30 kDa, preferably from about 2 kDa to 20 kDa. A linker may also be a natural or unnatural amino acid of at least 80 units in length.

PEG alternatives for the linker include synthetic or natural water-soluble biocompatible polymers such as polyethylene oxide, polyvinyl alcohol, polyacrylamide, proteins such as hyaluronic acid and chondroitin sulfate, celluloses such as hydroxymethyl cellulose, polyvinyl alcohol, and polyhydroxyalkyl (meth)acrylates.

Proteins and peptides may be covalently bound to the linker using conventional chemistries. Primary amine groups, such as found at the N-terminus or in lysine residues, will react with aldehydes and their equivalents under reductive conditions to give amines. (Molineux, *Current pharmaceutical design*, 10(11):1235-1244 (2004)). Mercapto (—SH) groups, such as found in cysteine residues, can undergo a conjugate addition with a variety of Michael acceptors, including acrylic and methacrylic acid derivatives, as well as maleimides (Gong et al., *British Journal of Pharmacology*, 163(2):399-412 (2011)). Other suitable nucleophilic groups found in peptides and proteins include disulfide bonds (Brocchini, et al., *Nature protocols*, 1:2241-2252 (2006)) and histidine residues (Cong, et al., *Bioconjugate Chemistry*, 23(2):248-263 (2012)).

The linker may be covalently joined to the protein or peptide using conventional chemistries. For instance, the linker polymer may be derivatized at one end with an electrophilic group such as an aldehyde, epoxide, halogen (chlorine, bromide, iodine), sulfonate ester (tosylate, mesylate), Michael acceptor, or activated carboxylates and then reacted with a nucleophilic amine or thiol group in the protein or peptide. Suitable Michael acceptors include acylic and methacrylic acid derivatives such as acrylamides, methacrylamides, acrylates and methacrylates, as well as maleimides. Suitable activated carboxylates include nitrophenyl carbonate and NHS (N-hydroxy succinate) esters. In other embodiments, peptides and proteins containing arginine residues may be covalently joined with a linker containing a reactive 1,3 diketone functional group.

The conjugates may be prepared by first joining the linker with the peptide or protein, followed by joining the linker with the branched poly(ethylene glycol), or by first joining the linker with the branched poly(ethylene glycol), followed by joining the linker with the peptide or protein. The optimal sequence of bond formation is determined by the specific chemical transformations involved.

Macromolecules

In other embodiments, TRAIL can be derivatized as a long-acting TRAIL with an extended half-life using biopolymers or polypeptides through reported methods; for example, but not limited to, using chemically conjugated hyaluronic acid (Yang et al., *Biomaterials* 32(33); 8722-8729 (2011), depot forming polypeptides (Amiram et al., *Proc natl Acad Sci USA.* 110(8); 2792-2792 (2013), U.S. Published Application No. US 2013-0178416 A1) and TRAIL linked to extended recombinant polypeptides (U.S. Published Application No. US 2010-0239554 A1).

Complexes

The TRAIL domain can be complexed with a negatively charged moiety. In some embodiments the negatively charged moiety can facilitate loading of the ligand or agonist into a nanoparticle for extended, sustained, or time released delivery. In some embodiments, the negatively charged moiety itself mediates extended, sustained, or time released delivery of the ligand or agonist. Preferably, the negatively charged moiety does not substantially reduce the ability of the ligand or agonist to induce or enhance apoptosis in immune cells or synoviocytes.

The formation of a complex between positively charged TRAIL and the negatively charged chondroitin sulfate (CS) (CS/TRAIL) was developed and shown to facilitate loading of TRAIL in poly(lactide-co-glycolide) (PLGA) microspheres (MSs), without compromising the activity of the TRAIL (Kim, et al., *Journal of Pharmacy and Pharmacology*, 65(1): 11-21 (2013). A nanocomplex of approximately 200 nm was formed in a weight ratio of 2 TRAIL to CS (TC2) at pH 5.0. The complex had >95% higher loading efficiency in PLGA MSs prepared by the multi-emulsion method than that of native TRAIL. Therefore, in some embodiments, the ligand or agonist, particularly TRAIL peptides, and variants, functional fragments and fusion proteins thereof, or conjugates thereof such as PEG-conjugates are complexed with chondroitin sulfate and optionally loaded into micro- or nanoparticles, for example, PLGA-based particles.

In other embodiments, the ligand or agonist, particularly TRAIL peptides, and variants, functional fragments and fusion proteins thereof, or conjugates thereof such as PEG-conjugates are complexed with hyaluronic acid (HA). Nanocomplexes of PEG-TRAIL and HA prepared by mixing positively charged PEG-TRAIL and negatively charged HA, were shown to have sustained delivery in vivo, with negligible loss of bioactivity compared with the PEGTRAIL (Kim, et al., *Biomaterials,* 31(34):9057-64 (2010)). Delivery was further enhanced by administering the nanoparticles in a 1% HA containing solution.

D. Targeting Moieties

The TRAIL-conjugate, compositions including the TRAIL-conjugate agent, and delivery vehicles for the TRAIL-conjugate agent can include a targeting moiety. In some embodiments, the targeting moiety increases targeting to or accumulation of the pro-apoptotic agent to the organ of interest or target cells.

In a preferred embodiment, the targeting moiety increases targeting to or accumulation of the pro-apoptotic agent in the liver and pancreas, and more preferably to hepatic stellate cells and pancreatic stellate cells. Compositions and methods for liver targeting are known in the art, see for example, U.S. Published Application No. 2013/0078216 which describes compositions and methods for targeting hepatocytes, and Poelstra, et al., *J. Control Release,* 161(2):188-97 (2012), which identifies target cells for each liver disease and reviews the strategies for drug delivery to these cells. The use of proteins, viruses, polymers and liposomes can all be employed to enhance targeting to the liver, or more preferably hepatic stellate cells. In some embodiments, the liver targeting molecules are fused with or conjugated to the pro-apoptotic agent itself, or to a composition that includes the pro-apoptotic agent, or delivery vehicles carrying the pro-apoptotic agent (e.g., a carrier such as a micro- or nanoparticle, liposome, etc.,).

The molecule can target a protein expressed in liver or in pancreas, or preferably on the surface of or in the microenvironment around hepatic stellate cells or pancreatic stellate cells. The target moiety can target a protein used in the art to identify hepatic stellate cells or pancreatic stellate cells. Preferably pro-apoptotic agents, compositions thereof, and vehicles for delivering them for treating liver diseases and liver fibrosis are (1) specifically targeted to activated HSCs, and preferably do not bind to myofibroblasts present in other tissues or quiescent HSCs; (2) can reach regions with active fibrogenesis; (3) are well tolerated by the immune system and not taken up nonspecifically by the reticuloendothelial system.

Exemplary targeting strategies include mannose-6-phosphate coupled to human serum albumin (M6P-HAS), which binds to the mannose-6-phosphate/insulin like growth factor II receptor, and a cyclic peptide coupled to HAS (pCVI-HAS) which recognizes the collagen type VI receptor (Beljaars, *Hepatology,* 29:1486-1493 (1999), and Beljaars, et al., *J Biol Chem.,* 275:12743-12751 (2000)). The structure of these proteins allows the coupling of additional chemical entities, which makes a selective delivery of antifibrotic agents to HSCs feasible. In another particular embodiment, the target is reelin, a large secreted extracellular matrix glycoprotein expressed by hepatic stellate cells and used histologically to distinguish them from other myofibroblasts.

The targeting moiety can be, for example, an antibody or antibody fragment such as immunoglobulin (antibody) single variable domains (dAbs) that binds to an antigen expressed in the liver, or more preferably on the surface of liver cells or in the microenvironment around hepatic stellate cells. The antibodies or antigen binding fragment thereof are useful for directing the conjugate to a cell type or cell state. In one embodiment, the ligand or agonist, composition that includes the ligand or agonist, or delivery vehicle possesses an antibody binding domain, for example, from proteins known to bind antibodies such as Protein A and Protein G from *Staphylococcus aureus*. Other domains known to bind antibodies are known in the art and can be substituted. The antibody binding domains can facilitate attachment of the targeting antibody to the ligand or agonist, or to a composition that includes the ligand or agonist, or delivery vehicle. In certain embodiments, the antibody is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art. In preferred embodiments, the targeting antibody or fragment thereof is specific for hepatic stellate cell surface marker, and are produced to reduce potential immunogenicity to a human host as is known in the art. For example, transgenic mice which contain the entire human immunoglobulin gene cluster are capable of producing "human"

antibodies can be utilized. In one embodiment, fragments of such human antibodies are employed as targeting signals. In a preferred embodiment, single chain antibodies modeled on human antibodies are prepared in prokaryotic culture.

E. Small Molecules and Peptidic Molecules

In some embodiments the pro-apoptotic agent is a small molecule or peptidic molecule that recognizes TRAIL-R1 and/or R2. Exemplary small molecules are known in the art and discussed in Wang, et al., *Nature Chemical Biology*, 9:84-89 (2013). The activity was initially discovered through a high-throughput chemical screen for compounds that promote cell death in combination with a small-molecule mimetic of Smac, the antagonist for inhibitor of apoptosis protein. Structure-activity relationship studies yielded a more potent analog called bioymifi, which can act as a single agent to induce DR5 clustering and aggregation, leading to apoptosis.

Monovalent, divalent, and trivalent TRAIL-mimicking peptides are described in Pavet, et al., *Cancer Research*, 70:1101-1110, (2010). Therefore, in some embodiments, the ligand or agonist of an agonistic TRAIL receptor is one or more of the mimics.

Dosages are expected to be in the same range as the compounds described above.

F. Ligand Conjugates

In an alternative embodiment, biopolymers or polysaccharides can be conjugated to the ligand or agonist. For example, the HA is conjugated to the ligand or agonist as in Yang, et al., *Biomaterials*, 32(33):8722-9 (2011). Yang describes a coupling reaction between an aldehyde modified HA and the N-terminal group of IFNα, which can be used to couple HA to the pro-apoptotic agents disclosed herein. The IFNα content can be controlled in the range of 2-9 molecules per single HA chain with a bioconjugation efficiency higher than 95%. The conjugates exhibit improved activity and half-life in vivo and increased delivery of IFNα to liver through targeting overexpressed CD44, HA receptor, in liver. HA can be used as a ligand targeting liver diseases and activated HSCs after coupled to the pro-apopotic agents (Kim, et al., *ACS Nano*, 4(6):3005-14 (2010)).

In some embodiments, the pro-apoptotic agent is modified to improve purification, Tag-removal, facilitate small molecule attachment or a combination thereof. Applied in tandem, elastin-like polypeptides and the Sortase A (SrtA) transpeptidase provide a method for chromatography-free purification of recombinant proteins and optional, site-specific conjugation of the protein to a small molecule (Bellucci, et al., *Angewandte Chemie International Edition*, 52(13):3703-3708 (2013)). This system provides an efficient mechanism for generating bioactive proteins at high yields and purities.

Other tags and labels are known in the art and include, for example, SUMO tags, His tags which typically include six or more, typically consecutive, histidine residues: FLAG tags, which typically include the sequence DYKDDDDK (SEQ ID NO:2); haemagglutinin (HA) for example, YPYDVP (SEQ ID NO:3); MYC tag for example ILKKATAYIL (SEQ ID NO:4) or EQKLISEEDL (SEQ ID NO:5). Methods of using purification tags to facilitate protein purification are known in the art and include, for example, a chromatography step wherein the tag reversibly binds to a chromatography resin.

Purifications tags can be at the N-terminus or C-terminus of the fusion protein. The purification tags can be separated from the polypeptide of interest in vivo (e.g., during expression), or ex vivo after isolation of protein. Therefore, purification tags can also be used to remove the fusion protein from a cellular lysate following expression.

The fusion protein can also include an expression or solubility enhancing amino acid sequence. Exemplary expression or solubility enhancing amino acid sequences include maltose-binding protein (MBP), glutathione S-transferase (GST), thioredoxin (TRX), NUS A, ubiquitin (Ub), and a small ubiquitin-related modifier (SUMO).

In some embodiments, fusion protein includes one or more linkers or spacers. In some embodiments linker or spacer is one or more polypeptides. In some embodiments, the linker includes a glycine-glutamic acid di-amino acid sequence. The linkers can be used to link or connect two domains, regions, or sequences of the fusion protein.

G. Formulations

In most cases, the TRAIL agonists are delivered systemically, most preferably by injection, or by implants, controlled release matrices, or coatings.

Pharmaceutical compositions including active agent(s) with or without a delivery vehicle are provided. Pharmaceutical compositions can be for administration by parenteral (intramuscular, intraperitoneal, intravenous (IV) or subcutaneous injection), enteral, or transmucosal (nasal, vaginal, rectal, or sublingual) routes of administration or using bioerodible inserts and can be formulated in dosage forms appropriate for each route of administration.

In certain embodiments, the compositions are administered locally, for example, by injection directly into a site to be treated (e.g., into the liver). In some embodiments, the compositions are injected or otherwise administered directly into the vasculature onto vascular tissue at or adjacent to the intended site of treatment (e.g., adjacent to the liver). Typically, local administration causes an increased localized concentration of the compositions which is greater than that which can be achieved by systemic administration.

Active agent(s) and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), antioxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

Active agents can be formulated for pulmonary or mucosal administration, for example, for treatment of pulmonary ischemia. In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs. Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. The suspension is sonicated to fully disperse the lipid molecules in the organic solvent. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

III. Methods of Treatment

The compositions are typically administered by injection, although in some embodiments they may be administered topically (as during surgery) or to a mucosal surface (rectally, vaginally, orally or pulmonarily). These may be administered in solution, in implants or gels, or as dry powders in dry form or redissolved or resuspended.

The Examples below illustrate that activated cells, such as hepatic stellate cells and pancreatic stellate cells, can be specifically targeted and killed by TRAIL-R1 (DR4) and/or TRAIL-R2 (DR5) agonists leading to TRAIL-induced apoptosis. Importantly, by eliminating such activated stellate cells, highly upregulated fibrosis-associated molecules were simultaneously down-regulated in fibrosis in vivo models. This demonstrates that the compounds can be used for treating pathological conditions in which activated fibroblasts, myofibroblastic cells, myofibroblasts, and activated endothelial and epithelial cells produce or induce an excess amount of extracellular matrix resulting in unwanted fibrosis or scarring are disclosed. The scarring or fibrosis can be in the liver, pancreas, lungs, heart, kidneys, intestine, skin or arteries.

Methods of specifically targeting, and reducing, inhibiting, and/or removing from the organs the activated fibroblasts, myofibroblastic cells, myofibroblasts, and excess extracellular matrix producing endothelial and epithelial cells are also provided.

As discussed in more detail below, the methods typically include administering to a subject with fibrosis or likely to develop fibrosis an effective amount of a pro-apoptotic agent to reduce the fibrosis, typically by inducing or increasing apoptosis of the cells underlying the fibrosis, cirrhosis, or complications thereof, such as ascites or pain. As used herein, "reduce" may be to reduce the size, the rigidity (as in scar tissue), or a combinations of factors understood by those skilled in the art.

A. Liver Disease

In one of the preferred embodiments, the composition and methods are used to treat liver disease. Liver fibrosis is characterized by excess extracellular matrix production, predominantly collagen type I, acting as an inflammatory response to chronic liver damage. The main causes of liver fibrosis in industrialized countries include chronic hepatitis C virus (HCV) infection, alcohol abuse and nonalcoholic steatohepatitis (NASH) (Bataller, et al., *Clin. Inves.*, 115(2): 209-18 (2005)). Progressive liver fibrosis eventually leads to cirrhosis and vasculature distortion further leading to liver failure, portal hypertension (PHT), hepatocellular carcinoma (HCC) and premature death. PHT can also trigger further complications such as gastrointestinal bleeding, ascites, encephalophathy, and reduced levels of platelets or decreased white blood cell count. A treatment of liver fibrosis and cirrhosis could provide a higher standard of care and reduce complications directly related to the fibrotic cascade. After removing the injury-causing factor in the liver, the fibrotic cascade progression can be slowed down or can regress. It was not until 1985 with the identification that hepatic stellate cells (HSCs) are the main culprit in ECM overexpression in the liver that potential therapeutics could be studied.

During chronic liver damage or disease, quiescent HSCs undergo activation and transform from a star-shaped vitamin, A-rich cells to highly proliferative, myoblast-like, vitamin A-deficient cells that take on fibrogenic properties (Bataller, et al., *Clin. Inves.*, 115(2):209-18 (2005); Friedman, et al., *Proc. Nat. Acad. Sci. USA;* 82(24):8681-5 (1985); Senoo, *Medical electron microscopy: official journal of the Clinical Electron Microscopy Society of Japan* 37(1): 3-15 (2004)). The activated HSCs express alpha-smooth muscle actin (alpha-SMA) and secrete type I collagen (Friedman, et al., *Proceedings of the National Academy of Sciences of the United States of America;* 82(24):86815 (1985); Rockey, et al., *Journal of submicroscopic cytology and pathology,* 24(2):193-203 (1992); Ramadori, et al., *Virchows Archiv B. Cell pathology including molecular pathology* 59(6):349-57 (1990)). The identification of activated HSCs, previously known as lipocytes, Ito cells or preisinusoidal cells, as the major fibrogenic cell type in liver injury along with the recognition of key cytokines involved in the process have provided numerous strategies for anti-fibrotic agents (Bataller, et al., *Clin. Invest.,* 115(2):209-18 (2005)).

Therapies have been tried to reduce the accumulation of activated HSCs to prevent excess ECM, which have been proven to be effective in experimental models (Wynn, et al., *Nature medicine.* 18(7):1028-40 (2012); Cohen, et al., *Ther. adv. gastroent.,* 4(6):391-417 (2011); Kisseleva, et al., *Best practice & research Clinical gastroenterology,* 25(2):305-17 (2011)). For example, renin-angiotensin system blockers and antioxidants can reduce the accumulation of scar tissue but have only shown efficacy in experimental models. There are currently many suggested strategies in the treatment of liver fibrosis and cirrhosis (Table 1 from Friedman, In: *Bruce A Runyon ACT, ed. UpToDatecom,* (2011)). Targeting activated HSCs or their activation, proliferation and function, is an important antifibrotic strategy (Friedman, *In: Bruce A Runyon ACT, ed. UpToDatecom,* (2011); Breitkopf, et al., *Clinical and Experimental Research,* 29:121S-31S (2005); Kisseleva, et al., *Journal of Gastroenterology and Hepatology,* 21:S84-S87 (2006)). HSC reversion has shown to promote fibrosis regression in animal models for many forms of hepatocellular injury (Kisseleva, et al., *Proc. Natl. Acad. Sci. USA,* 109(24):9448-53 (2012); Troeger, et al., *Gastroenterology,* 143(4): 1073-83 (2012)). However, even if HSC activation and fibrogenesis is terminated, reverted HSCs have a higher responsiveness to recurrent fibrogenic stimulation, indicating that these HSCs do not completely revert to a quiescent state (Troeger, et al., *Gastroenterology,* 143(4): 1073-83 (2012)). Another proposed manner is the elimination of activated HSCs that favor apoptosis over reversion (Bataller, et al., *Semin Liver Dis,* 21(03):437-52 (2001); Friedman, *Proc. Natl. Acad. Sci. USA,* 109(24): 9230-1 (2012)).

This is further validated in a model of spontaneous recovery from liver fibrosis in rats, where apoptosis of activated HSCs was the vital contribution to resolution of fibrosis (Iredale, et al., *J Clin Invest,* 102(3):538-49 (1998)). Activated HSCs in this model were shown to be responsible for producing the fibrotic matrix as well as protecting the matrix from degradation by producing tissue inhibitors of metalloproteinase (TIMPs). Importantly, however, the literature reports the absence of therapeutic approaches to promote apoptosis specifically in hepatic stellate cells, such as the method disclosed herein.

B. Methods of Treating Liver Disease

Methods of treatment typically include administering to a subject in need thereof an effective amount of a pro-apoptotic agent, for example, one or more ligands or agonists of an agonistic TRAIL receptor, to induce or increase apoptosis of one or more target cells types such as hepatic stellate cells, fibromyoblasts, fibromyoblastic cells, activated endothelial cells or activated epithelial cells that produce or induce an excess amount of extracellular matrix resulting in unwanted scarring of the liver in the subject. In a preferred embodiment the target cells are hepatic stellate cells.

Typically, the pro-apoptotic agent is administered to the subject in an effective amount to increase apoptosis of one or more of the target cell types. Preferably, the level of apoptosis is effective to reduce or inhibit the onset or progression of liver disease, or one or more symptoms thereof. For example, in some embodiments, the pro-apoptotic agent is administered in effective amount to reduce fibrosis or increase fibrosis regression, reduce the accumulation of scar tissue, reduce fibrotic cascade progression, reduce the accumulation of extracellular matrix, reduce cirrhosis, or a combination thereof.

Hepatic stellate cell apoptosis and the resolution of liver fibrosis can be assessed in the subject using a number of techniques. Overall improvement in the liver disease that the subject is suffering from may also be seen. The condition of the subject and liver function in the subject can be assessed to monitor any lessening in the severity of, or the disappearance altogether, of one or more symptom associated with liver disease and in particular with liver fibrosis. For example, whether or not there is any change in jaundice, fluid retention, ease of bruising, frequency of nose bleeds, skin or nail condition may be assessed. The general well-being of the subject can improve and this may be assessed as an indicator of recovery. The subject can display increased appetite, reduction in the incidence, or severity of, nausea, increase in weight and/or general feelings of strength and energy. The subject can also have reduced incidence of hospitalization or need of other medical attention.

The liver function of the subject can be improved or increased. Liver function can be stabilized. This may be assessed in a variety of ways. Liver biopsies or blood samples can be taken and markers of liver function can be determined. Markers of liver function which can be studied include hyaluronic acid, procollagen IIIN peptide, procollagen IC peptide, Undulin-collagen 16, 7S type IV collagen, MMP-2 and TIMP-1 levels.

The subject's liver can show decreased nodulization, necrosis, inflammation, or a combination thereof. In particular, the liver of the subject can display a decrease, or stabilization, in the amount of fibrosis in their liver. The presence of fibrotic material in the liver can be decreased and this can be determined by staining sections from liver biopsies using stains such as Sirius red. The presence and amount of particular fibrotic extracellular matrix components such as, for example, collagens and in particular collagens I and III may be determined. Biochemical analyses can also be carried out to determine levels of TIMPs and/or MMPs and the reduction of TIMP expression in the subject.

The apoptosis of hepatic stellate cells in the liver may also be determined from liver biopsies. Any change, and in particular any increase, in the frequency of apoptosis of hepatic stellate cells may be measured. Apoptotic cells can be identified using a number of well-known methods. Techniques such as TUNEL staining (terminal deoxynucleotidyl transferase mediated deoxyuridine trisphosphate nick end labelling) can be used to identify apoptotic cells. TUNEL staining is particular useful as it can be used to identify apoptotic cells in situ. Through co-staining it can be checked that the cells undergoing apoptosis are hepatic stellate cells such as by staining for α-smooth muscle actin expressing cells.

Other well-known techniques for identifying and/or quantifying apoptosis can be employed such as, for example, Annexin V staining, antibodies against single stranded DNA, caspase substrate assays, ligation mediated PCR and cell membrane permeability staining. DNA fragmentation can be analyzed by gel electrophoresis. Staining can also be used to determine the morphological characteristics associated with apoptosis, such as membrane blebbing and the breakdown of the nucleus. Acridine orange staining can be used to identify apoptotoic cells. Cells may be stained with propidium iodide to analyze DNA content. Tests such as trypan blue staining can be used to check that the membrane cell is intact and that they are apoptotic not necrotic.

The effect of administration of the pro-apoptotic agent can be compared to a control. Suitable controls are known in the art and include, for example, a matched untreated subject, or a matched subject administered a therapeutic agent that does not induce or increase apoptosis of the target cells.

The compositions can be administered locally or systemically, as discussed above. In a particular embodiment, the composition is administered to the subject by percutaneous injection into the liver. The injection can be into and/or adjacent to a site of fibrosis or scarring in the liver, a site of excess extracellular matrix accumulation, a site of activated or proliferating HSC, or a site of another biochemical, histological, or morphological marker of diseased liver. As discussed in more detail below, the compositions can be administered alone or in combination with additional active agents.

IV. Combination Therapies

One or more of the pro-apoptotic agents disclosed herein, and compositions thereof, can be administered to subjects in need thereof alone, or in combination, with one or more additional active agents. In some embodiments, the second active agent is an agent that is known in the art for treatment of a fibrotic disease, particularly liver fibrotic disease. In some embodiments, the second active agent is one that modulates hepatic stellate cells, for example, an agent that reduces hepatic stellate cell proliferation, reduces hepatic stellate cell activation or activity, increases stellate cell apoptosis, reduces deposition of extracellular matrix or components thereof, particularly collagen, increases degradation of extracellular matrix or components thereof, particularly collagen, or any combination thereof. In some embodiments, the second active agent increases the efficacy, enhances the effect, or otherwise improves the performance or sensitive of cells to the ligand or agonist.

In some embodiments, the second active agent is not related to modulation of hepatic stellate cells. For example, in some embodiments, the second agent reduces liver inflammation. In some embodiments, the second active agent can be an agent that treats or reduces one or more symptoms of liver fibrosis without effecting the proliferation, activity, activation, or apoptosis of hepatic stellate cells.

Exemplary additional therapeutic agents include, but are not limited to, glycyrrhizin, halofuginone, hepatocyte growth factor (HGF), HOE 077, interferon-α, interferon-γ, interleukin-10, malotilate, pentoxifylline, phosphatidylcholine, S-adenosyl-L-methionine (SAMe), saturated fatty acids, Sho-saiko-to, Sylimarin, transforming growth factor β (TGF-β) inhibitors, TNP 470, tocopherol, trichostatin A, and urokinase-type plasminogen activator (uPA) (Bataller, et al., *Semin Liver Dis.*, 21(3) (2001).

A. Second Active Agents

1. Antioxidants

The second or subsequent active agent can be an antioxidant. Exemplary antioxidants include, but are not limited to, vitamin E (α-tocopherol), Silymarin (a flavonoid antioxidant extracted from Silybum marianum), phosphatidylcholine (PPC), S-adenosyl-L-methionine (SAMe), retinoids (retinyl palmitate) and natural phenolic compounds (resveratrol and quercetin).

2. Agents that Inhibit HSC Migration or Interaction with the Surrounding Extracellular Matrix In some embodiments, the second or subsequent active agent is an agent that reduces or inhibits migration of hepatic stellate cells, or interaction between the cells and their microenvironment, for example, the surrounding or underlying extracellular matrix. Stimulation of HSCs with platelet-derived growth factor (PDGF)-BB, transforming growth factor (TGF)-beta1, and/or epithelial growth factor (EGF) increase the migratory capacity and up-regulate matrix metalloproteinase (MMP)-2 activity (Yang, et al., *Gastroenterology*, 124(1):147-59 (2003)). Migration induced by PDGF-BB is believed to be associated with increased proliferation, while TGF-beta1/EGF-induced migration appears to be proliferation independent. Yang, et al., (supra) also reports that COL-3, an inhibitor of MMP-2 and MMP-9, inhibited migration of HSCs induced by direct activation of PDGF-BB or TGF-beta1 but had no effect on migration induced by chemotactic stimuli without direct contact, indicating two distinct MMP-dependent and MMP-independent mechanisms of PDGF-BB- or TGF-beta1-induced migration.

Therefore, in some embodiments, the second active agent is an agent that reduces or inhibits PDGF-BB-induced migration, TGF-beta1-induced migration, or a combination thereof. An exemplary inhibitor of is COL-3, which has been the subject of clinical trial. A phase 1 trial included administering subjects with COL-3 doses escalating from 36 mg/m$^2$/d, and found a maximum tolerated dose of 98 mg/m$^2$/d and well tolerated at 70 mg/m$^2$/d.

Migration induced by PDGF-BB, TGF-beta1, and collagen I can also be inhibited by alpha(1)- and/or alpha(2)-integrin blocking antibodies and competitive RGD antagonists, and studies show that curcumine inhibits migration and invasion of activated HSC by reducing MMP-2 expression and activity (Huang, et al., *Zhonghua Gan Zang Bing Za Zhi,* 17(11):835-8 (2009). Other evidence indicates that the interferon-α and γ can also inhibit HSC, or increase their apoptosis (Weng, et al., *J Hepatol.,* 59(4):738-45 (2013) and (Glassner, et al., *Lab Invest.,* 92(7):967-77 (2012)).

3. Agents that Inhibit Liver Inflammation

In some embodiments, the second or subsequent active agent is an agent that reduces or inhibits liver inflammation. Exemplary anti-inflammatories include, but are not limited to, corticosteroids, colchicine, and malotilate.

In some embodiments, the second or subsequent active agent is an agent that reduces or inhibits the activity of a proinflammatory factor or cytokine. For example, the agent can be an interleukin-1 receptor antagonist, or soluble tumor necrosis factor-α (TNF-α) receptors can reduce necrosis and inflammation in liver tissue. Additionally, IL-10 has been shown to downregulate proinflammatory Thi responses. Patients with chronic HCV infection treated with recombinant interleukin-10 showed not only an improvement of liver inflammation, but also resolution of the initial deposition of fibrous scar (Louis, et al., *Hepatology,* 28:1607-1615 (1998)).

4. Agents that Inhibit of TGF-β Activity

In some embodiments, the second active agent inhibits TGF-β activity. Approaches used to prevent the binding of TGF-β to its receptors include the use of a dominant-negative type II TGF-β receptor, the expression of the ectodomain of type II receptor fused to the Fc portion of human IgG, the expression of a truncated type II receptor, and the construction of a soluble type II receptor. HGF either as a recombinant protein or by gene therapy is also effective in preventing the progression of liver fibrosis in different experimental models, and can be used to modulate HSC proliferation, collagen formation, and TGF-b expression, without the potential drawbacks and dangers of prolonged systemic or global inhibition of TGF-β.

In some embodiments, the second active agent is a microRNA or a mimic thereof. Members of the miR-17-92 cluster (19a, 19b, 92a) are significantly down-regulated in activated HSCs (Lakner, et al., *Hepatology,* 56(1):300-10 (2012)). In particular, miR 19b mimic negative regulation of TGF-β signaling components has been demonstrated by a decreased TGF-β receptor II (TGF-βRII) and SMAD3 expression, binding of miR 19b to the 3' untranslated region of TGF-βRII, inhibition of TGF-β signaling, decreased expression of type I collagen and blocking TGF-β-induced expression of α1(I) and α2(I) procollagen mRNAs. miR 19b also blunted the activated HSC phenotype by morphological assessment and decreased smooth muscle α-actin expression. Therefore, in a preferred embodiment the microRNA is a miR 19b or a mimic thereof.

5. Chemotherapeutic Agents

Ligands of agonistic TRAIL receptors have been investigated for use in the treatment of cancer, both alone and in combination with conventional cancer treatments such as chemotherapeutic agents. Some reports indicate that chemotherapeutic drugs can sensitize cells to TRAIL-induced apoptosis, and some results indicate that the combination of the two agents is more effective the sum of effects of the agents when used alone (Cuello, et al., *Gynecol Oncol.,* 81(3):380-90 (2001) Wu, et al., *Vitam Horm.,* 67:365-83 (2004)). Therefore, in some embodiments, the subjects and diseases disclosed herein are treated with a combination of a ligand or agonist of an agonistic TRAIL receptor and a chemotherapeutic agent. In some embodiments, the subjects do not have cancer.

Exemplary chemotherapeutic drugs include, but are not limited to, doxorubicin, 5-fluorouracil, cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

B. Dosage and Treatment Regimes for Combination Therapies

The methods of treatment disclosed herein typically include treatment of a disease or symptom thereof, or a method for achieving a desired physiological change, including administering to an animal, such as a mammal, especially a human being, an effective amount of a pro-apoptotic agent to treat a liver disease or symptom thereof, or to produce the physiological change. In some embodiments, the pro-apoptotic agent is in combination with an additional active agent. The pro-apoptotic agent and the additional active agent can be administered together, such as part of the same composition, or administered separately and independently at the same time or at different times (i.e., administration of the ligand or agonist and the second active agent is separated by a finite period of time from each other). Therefore, the term "combination" or "combined" is used to refer to either concomitant, simultaneous, or sequential administration of the ligand or agonist and the second active agent. The combinations can be administered either concomitantly (e.g., as an admixture), separately but simultaneously (e.g., via separate intravenous lines into the same subject; one agent is given orally while the other agent is given by infusion or injection, etc.), or sequentially (e.g., one agent is given first followed by the second).

In preferred embodiments, administration of the pro-apoptotic agent in combination with the second active agent achieves a result greater than when the pro-apoptotic agent and the second active agent are administered alone or in isolation (i.e., the result achieved by the combination is more than additive of the results achieved by the individual components alone). In some embodiments, the effective amount of one or both agents used in combination is lower than the effective amount of each agent when administered separately. In some embodiments, the amount of one or both agents when used in the combination therapy is sub-therapeutic when used alone.

A treatment regimen of the combination therapy can include one or multiple administrations of ligand or agonist. A treatment regimen of the combination therapy can include one or multiple administrations of the second active agent.

In some embodiments, the pro-apoptotic agent is administered prior to the first administration of the second active agent. In other embodiments, the ligand or agonist is administered after to the first administration of the second active agent.

The ligand or agonist can be administered at least 1, 2, 3, 5, 10, 15, 20, 24 or 30 hours or days prior to or after administering of the second active agent.

Dosage regimens or cycles of the agents can be completely, or partially overlapping, or can be sequential. For example, in some embodiments, all such administration(s) of the pro-apoptotic agent occur before or after administration of the second active agent. Alternatively, administration of one or more doses of the pro-apoptotic agent can be temporally staggered with the administration of second therapeutic agent to form a uniform or non-uniform course of treatment whereby one or more doses of pro-apoptotic agent are administered, followed by one or more doses of second active agent, followed by one or more doses of pro-apoptotic agent; or one or more doses of second active agent are administered, followed by one or more doses of the pro-apoptotic agent, followed by one or more doses of second active agent; etc., all according to whatever schedule is selected or desired by the researcher or clinician administering the therapy.

An effective amount of each of the agents can be administered as a single unit dosage (e.g., as dosage unit), or sub-therapeutic doses that are administered over a finite time interval. Such unit doses may be administered on a daily basis for a finite time period, such as up to 3 days, or up to 5 days, or up to 7 days, or up to 10 days, or up to 15 days or up to 20 days or up to 25 days.

V. Kits

Medical kits are also disclosed. The medical kits can include, for example, a dosage supply of an pro-apoptotic agent, preferably a ligand or agonist for an agonistic TRAIL receptor, alone or in combination with a second therapeutic agent. When in combination with a second therapeutic agents, the active agents can be supplied alone (e.g., lyophilized), or in a pharmaceutical composition (e.g., an admixture). The active agents can be in a unit dosage, or in a stock that should be diluted prior to administration. In some embodiments, the kit includes a supply of pharmaceutically acceptable carrier. The kit can also include devices for administration of the active agents or compositions, for example, syringes. The kits can include printed instructions for administering the compound in a use as described above.

The present invention will be further understood by reference to the following non-limiting examples.

EXAMPLES

Example 1: Expression of TRAIL-R1/DR4 and TRAIL-R2/DR5 by Activated Human Primary Hepatic Stellate Cells (HSCs) and Pancreatic Stellate Cells (PSCs)

Materials and Methods
Human Primary Stellate Cells

Human primary HSCs, PSCs and stellate cell medium (SteCM) were obtained from ScienCell Research Laboratories (Carlsbad, Calif.). Cells were cultured in SteCM medium supplemented with 2% of FBS, 1% of stellate cell growth supplement and 1% of penicillin/streptomycin solution in poly-1-lysin coated plates. To activate primary stellate cells, cells were then cultured in 6 well plastic culture plates for 1, 4, 7 and 14 days and harvested. The expression of DR-4, DR-5 and α-SMA in cultured stellate cells were determined by Western blot analysis and real time PCR.

Comparative Quantitative Real Time RT-PCR

Total RNA from cultured cells was extracted with TRIzol reagent (Life Technologies, Grand Island, N.Y.) and was reverse transcribed to cDNA using the Reverse Transcription System (Life Technologies, Grand Island, N.Y.). Comparative quantitative real time PCR was performed in duplicate for each sample with a StepOnePlus Real-Time PCR System (Life Technologies, Grand Island, N.Y.) using SYBR Green Master Mix (Life Technologies, Grand Island, N.Y.) according to the manufacturer's instructions. The expression levels of target genes were normalized to the expression of GAPDH and calculated based on the comparative cycle threshold Ct method ($2^{-\Delta\Delta Ct}$). Collagen 1 and α-SMA, TGF-β, Timp-1, TRAILR1/DR-4, and TRAILR2/DR-5 primers were used for the PCR.

Western Blot Analysis

Cultured cells were washed three times with ice cold PBS and harvested in cold lysis buffer with protease inhibitors (Santa Cruz Biotechnology, Dallas, Tex.). Cells were then sonicated and centrifuged, and the supernatant was measured for protein concentration. Anti-α-SMA (Sigma Aldrich, St. Louis, Mo.), anti-TGF-β (Cell signaling, Beverly, Mass.), anti-DR-4 (Santa Cruz Biotechnology, Dallas, Tex.) and anti-DR-5 (Abcam. Cambridge, Mass.) were used for the markers of activated stellate cell and liver fibrosis. Anti-cleaved PARP-1 (Cell signaling) was used as a marker for apoptosis. Anti-β-actin antibody (Sigma Aldrich, St. Louis, Mo.) was used for protein loading control.

Results

Human primary HSCs and PSCs gradually activate from the time of plating and progressively express DR4 and DR5. To ascertain gene expression of TRAIL-R1/DR4 and TRAIL-R2/DR5, real-time PCR was performed in cultured cells. The gene expression of DR4 and DR5 were gradually increased along with the activation of HSC and PSC. mRNA expression was assessed using real-time PCR. Based on real-time PCR analysis, α-SMA, a marker of stellate cell activation, collagen 1, TGF-β, and MMP-2, 9, 13 and Timp-1 were up-regulated in early activated (day 4) and fully activated (day 7 and 14) stellate cells but undetected during the quiescence stage of cells. Protein levels of TRAIL-R1/DR4 and R2/DR5 confirmed by Western blot analysis were also induced in highly activated stellate cells but not in quiescent cells. Similarly, alpha-SMA (α-SMA) was undetected at day 0 in cultured cells but was strongly enhanced after cultured cells at day 4 and 7. β-actin controls were equally present at day 0, 4, and 7. Expression of DR5 and α-SMA during HSC activation was confirmed (data not shown). This result demonstrates that HSCs and PSCs initiate expression of death receptors or overexpress existing death receptors during the activation process.

Example 2: Activated Human Primary HSCs and PSCs Demonstrate Enhanced Sensitivity to TRAIL Agonist-Induced Apoptosis Materials and Methods
Immunofluorescence Staining of Apoptosis Cells were plated on glass coverslips in 35 mm culture dishes (MatTek corporation, Ashland, Mass.) and grown for 1, 4, 7, and 14 days. Cells were then treated with or without TRAIL agonists including 1 microgram/ml (μg/ml) of TRAIL, PEGTRAIL or 50 ng/ml of anti-DR5 antibody (R&D systems, Minneapolis, Minn.) for 3 hours on those days. Cells were washed twice with cold PBS and fixed in 4% paraformaldehyde in PBS for 10 minutes. For detection of apoptosis, TdT In Situ Apoptosis Detection Kit (TUNEL)-Fluorescein (R&D systems, Gaithersburg, Md.) was used according to the manufacturer's instruction. Briefly, cells were incubated with proteinase K for 15 minutes at room temperature, then washed twice with DW, immersed with TdT labeling buffer, and then incubated with TdT labeling reaction mix at 37° C. for 1 hour. Next, cells were treated with TdT stop buffer to stop the labeling reaction and washed twice with DW. Finally, Step-Fluor solution was added, and cells were incubated for 20 minutes at RT and washed twice with PBS. Fluorescence Mounting Medium with DAPI (Vector Laboratories, Burlingame, Calif.) was applied to the samples. Samples were viewed under a fluorescence microscope using a 495 nm filter for apoptosis and a 358 nm filter for DAPI.

Western Blot Analysis

Cultured cells were washed three times with ice cold PBS and harvested in cold lysis buffer with protease inhibitors (Santa Cruz Biotechnology, Dallas, Tex.). Cells were then sonicated and centrifuged, and the supernatant was measured for protein concentration. Anti-cleaved PARP-1 (Cell signaling) was used as a marker for apoptosis. Anti-β-actin antibody (Sigma Aldrich, St. Louis, Mo.) was used for protein loading control.

Cell Viability (MIT Assay)

HSCs and PSCs were plated in a 48-well flat bottom plates and cultured for 1, 4, 7, and 14 days. On day 1, 4, 7, 14 the cells were incubated with TRAIL, PEG-TRAIL and TRAIL agonistic antibody, an anti-DR5 antibody for 3 hours at 37° C. At the indicated times, a final concentration of 5 μg/ml MTT solution were added to each well for 1 h. After removal of the medium, 200 ml of DMSO was added to each well to dissolve the formazan crystals. The absorbance at 590 nm was determined using a microplate reader (Bio-Tek Instruments, Inc, Winooski, Vt.). Triplicate wells were assayed for each condition.

Results

Activated human primary HSCs and PSCs demonstrated enhanced sensitivity to TRAIL-induced apoptosis. HSCs and PSCs were incubated with TRAIL, PEG-TRAIL and TRAIL agonistic antibody, an anti-DR5 antibody for 3 hours after 1, 4, 7 and 14 days of culturing in media, respectively. Highly activated HSCs and PSCs (at day 7 and 14) are more susceptible than less activated HSCs and PSCs (at day 1 and 4) as shown by an increase in TUNEL fluorescence observed in cells treated with TRAIL after 7 and 14 days compared to control cells as well as apoptotic cells by taking pictures directly from cell culture plates with a bright field microscope (Nikon metrology, Brighton, Mich.). In addition, protein levels of cleaved PARP-1, an apoptosis marker, were confirmed by Western blot analysis. When TRAIL agonists were treated in activated HSCs and PSCs at day 7 and 14, expression of cleaved PARP-1, an apoptosis marker, was clearly observed as evidence of TRAIL-induced apoptosis in activated stellate cells.

To quantitatively analyze TRAIL sensitivities of activated HSCs and PSCs against TRAIL agonists, TRAIL sensitivity was expressed as the induced cell death (%), calculated as the percentage relative to the untreated cells, and measured by MTT assays following 3 h incubations. TRAIL, PEG-TRAIL and TRAIL agonistic antibody induced strong TRAIL-mediated apoptosis in activated HSCs and PSCs at day 7 and 14 (shown in Example 1 to be highly activated at those time points), but showed marginal effects in quiescent cells at day 1. In HSCs, when TRAIL agonists were treated on day 7 and day 14 of activation, TRAIL, PEG-TRAIL and anti-DR5 antibody induced 4.5, 4.1, 4.4-fold and 7.5, 6.2, 5.2-fold increase in cell death compared to that of cells treated at day 1 (FIG. 1). Similarly, in PSCs, TRAIL, PEG-TRAIL and anti-DR5 antibody induced 5.5, 4.7, 5-fold increase in cell death from day 1 to day 14. These results clearly shows that activated HSCs and PSCs, originators of fibrotic liver and pancreatic diseases, can be specifically targeted and removed by treating them with TRAIL agonists.

Example 3: Treatment with TRAIL Prevents Liver Fibrosis

Materials and Methods

Liver Fibrosis Induced by CCl4 in Rats (Group 1)

Figure 2:
FIG. 2 is an illustration of an experimental design showing the injection schedule of CCl4, CCl4 and TRAIL, CCl4 and PEG-TRAIL, respectively in weeks of treatment. Group 1 schedule was used to examine if PEG-TRAIL prevents fibrogenesis, Group 2 schedule was used to examine if PEG-TRAIL reverses liver fibrosis and Group 3 schedule was used to investigate if PEG-TRAIL ameliorates liver cirrhosis.
Figure 2:
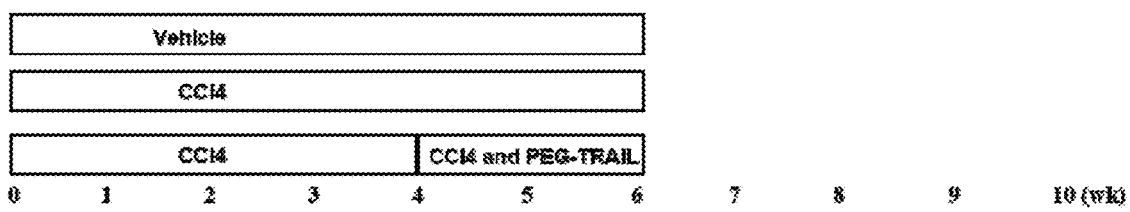
Figure 2:
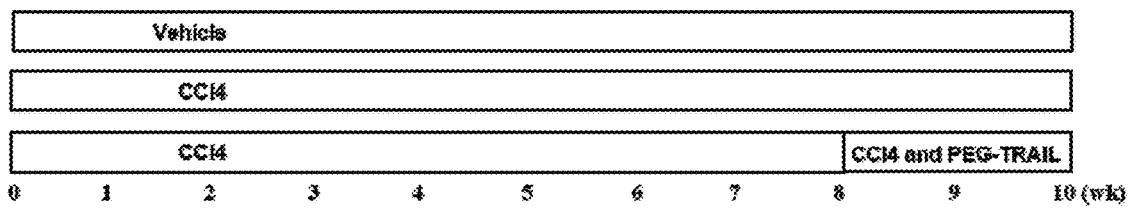

6-8 week old SD rats (Hanlim Experimental Animal Laboratory, Seoul, Korea) were divided into 3 groups (8-10 rats per group); i) vehicle (olive oil), ii) 20% CCl4 in olive oil and iii) CCl4 in olive oil and TRAIL (Group 1, FIG. 2). Rats were administered CCl4 (20% CCl4 in olive oil, 2 ml/kg) three times per week via intraperitoneal injection or olive oil as a control for 4 weeks while simultaneously being treated with 4 mg/kg of intravenously administered TRAIL every three days or with the same amount of saline for control groups (Group 1, FIG. 2).

Liver Histology and Immunohistochemistry of Liver Fibrosis

After treatment, animals were sacrificed and collected liver tissues were fixed in 10% buffered formalin, embedded in paraffin, and cut into 4 m thick sections. The sections were then stained with hematoxylin and eosin (H&E). Immunohistochemistry was performed with α-SMA (DakoCytomation, Carpinteria, Calif.) antibody for detecting activated HSCs. Histostain-Plus Kit (Life Technology) was used for all procedures of immunohistochemistry. Briefly, liver sections were deparaffinized, hydrated, quenched in 3% of hydrogen peroxide solution and washed on slides. Slides were applied with blocking solution and sequentially applied to primary α-SMA antibody and biotinylated second antibody followed by an enzyme conjugated reagent. Liver section slides were developed by 3, 3'diaminobenzidine (DAB) via a chromogen/substrate kit (Vector Laboratories, Burlingame, Calif.). For detection of collagen deposition, liver sections were stained with Sirius red staining solution (Sigma, St. Louis, Mo.) and washed in 5% acetic acid water. Stained liver tissues were visualized under light microscopy (Olympus America).

Immunofluorescence Analysis of HSC Apoptosis in Fibrotic Liver

Liver sections were immunostained by primary antibodies, α-SMA (Dakocytomation) and caspase-3 (Cell signaling) antibodies, and secondary antibodies, anti-mouse Alexa Fluor 488 and anti-rabbit Alexa Fluor 546, and mounted with Fluorescence Mounting Medium with DAPI (Vector Laboratories. Burlingame, Calif.). Sections were viewed under a fluorescence microscope and images were recorded.

Results

H&E and immunohistochemical analyses of α-SMA and Sirius red stain (collagen deposition marker) in the liver tissues from control, CCl4, CCl4 and TRAIL showed that TRAIL treatment significantly prevents and inhibits liver fibrosis. The liver tissues from rats treated with CCl4 without TRAIL revealed strong signals of α-SMA and Sirius red indicating signs of fibrogenesis in the liver. In contrast, rats simultaneously treated with CCl4 and TRAIL showed significant reduction in fibrosis as evidenced by reduced α-SMA and collagen in the liver (data not shown). This result indicates that TRAIL agonists like TRAIL effectively prevents induction of liver fibrosis in vivo.

To confirm if such preventive effect is induced by TRAIL-induced apoptosis in activated HSCs, immunofluorescence analyses were performed for α-SMA, caspase-3 (apoptosis marker) and DAPI (nucleus) in liver tissues from rats treated with CCl4 and saline, CCl4 and TRAIL, and control groups. α-SMA (Alexa Fluor 488, green) was detected in both CCl4 and saline group and CCl4 and TRAIL treated group whereas caspase-3 (Alexa Fluor 546, red) was not detected in TRAIL-treated normal liver tissues and CCl4-treated fibrotic liver tissues. In contrast, when TRAIL was treated in fibrotic liver tissues, strong apoptotic signals from caspase-3 were observed. In particular, expressed caspase-3 co-localizes with α-SMA, an activated HSC marker, and confirms that TRAIL specifically induces apoptosis in activated HSCs.

Example 4: The Treatment with PEGylated TRAIL Reverses Liver Fibrosis

Materials and Methods

Liver Fibrosis Induced by CCl4 in Rats (Group 2)

6-8 week old SD rats (Hanlim Experimental Animal Laboratory) were divided into 3 groups (8-10 rats per group); i) vehicle (olive oil), ii) 20° % CCl4 in olive oil and iii) CCl4 in olive oil and PEG-TRAIL. Rats were administered CCl4 (2 ml/kg) three times per week via intraperitoneal injection or olive oil as control groups for 4 weeks. After induction of liver fibrosis totaling 4 weeks, rat were treated with 4 mg/kg of intravenously administered PEG-TRAIL every other day for 2 weeks while continuing CCl4 or olive oil injections (Group 2, FIG. 2).

Western Blot Analysis

The rapidly frozen liver tissue was placed in a porcelain mortar and pestle and ground to a fine powder while still at liquid nitrogen temperature. The fine powder was then lyzed with sonication briefly in ice-cold PBS buffer (1 mM PMSF, and 1 µg/ml each of aprotinin, leupeptin, and pepstatin A). Cell lysates were clarified by centrifugation with 14,000 rpm at 4° C. The concentration of the protein was measured by Bradford solution (Bio-Rad, Hercules, Calif.). Same amount of protein was resolved by SDS-PAGE, and proteins on gels were transferred to nitrocellulose (Bio-Rad, Hercules, Calif.) using a semidry blotter (Bio-Rad). The membrane was blocked with 3% BSA in TBST (10 mM Tris-Cl, pH 8.0, 150 mM NaCl, 0.5% Tween-20) and incubated overnight at 4° C. with primary antibodies. Anti-DR4 (Abcam, Cambridge, Mass.), anti-DR5 (Abcam), anti-Caspase-8 (Cell Signaling Technology, Danvers, Mass.), anti-cleaved PARP-1 (Cell Signaling Technology), anti-cleaved Caspase-3 (Cell Signaling Technology), anti-cleaved Caspase-9 (Cell Signaling Technology), anti-alpha SMA (Sigma), anti-MMP-2 (Santa Cruz Biotechnology), anti-Collagen 1 (Cell Signaling Technology), anti-TGF-β (Abcam), anti-TIMP-1 (Millipore, Billerica, Ma), anti-PDGFR-β (Santa Cruz Biotechnology), anti-GAPDH (Santa Cruz Biotechnology), and anti-β-actin (Santa Cruz Biotechnology) were used in western blot analysis. Immunoblots were visualized by enhanced chemiluminescence method.

Quantitative Real Time PCR (qPCR)

Total RNA from cultured cells and rat liver tissues was extracted with TRIzol reagent (Life Technologies, Grand Island, N.Y.) following the instruction provided by the company. RNA concentration was measured spectrophotometrically by using NanoDrop 2000 (Thermo Fisher Scientific, Waltham, Mass.). 1-2 µg of total RNA were reverse-transcribed to cDNA using the High-Capacity cDNA Reverse Transcription System (Life Technologies). qPCR was performed in duplicate or triplicate for each sample using fast SYBR Green Master Mix (Life Technologies) and StepOnePlus Real-Time PCR System (Life Technologies). The expression levels of target genes were normalized to the expression of GAPDH and calculated based on the comparative cycle threshold Ct method ($2^{-\Delta\Delta C_t}$). qPCR for rat liver samples was performed using RT2 qPCR Primer set (Qiagen, Valencia, Calif.); Col1a2 (PPR56530A), Acta2 (PPR59337B), Mmp3 (PPR48487B), Col3a1 (PPR43017A), Mmp9 (PPR44728C), Mmp13 (PPR45162A), Timp1 (PPR48051C), Timp3 (PPR06533A), Gapdh (PPR06557B), Tgfb1 (PPR06430B), Tgfb3 (PPR06467C), Tgfbr2 (PPR06488E) and Bmp7 (PPR46571A) (RT2 qPCR Primer Assay, SABiosciences, Quiagen).

Other Biomarker Analysis

Hydroxyproline, a maker of collage deposition in liver, assay using liver tissues was measured by a Hydroxyproline Assay Kit (Sigma, MAK008-1KT) according to the manufacturer's instructions. Rat blood was collected by cardiac puncture, placed at room temperature for 2 h and centrifuged at 3000 rpm for 20 min. Routine liver function tests analyzed in serum included alanine aminotransferase (ALT), aspartate aminotransferase (AST), total protein, albumin, alkaline phosphatase (ALP) total bilirubin, and direct bilirubin.

Liver Histology and Immunohistochemistry of Liver Fibrosis

Liver tissues were fixed in 10% buffered formalin, embedded in paraffin, and cut into 4 m thick sections. The sections were then stained with hematoxylin and eosin (H&E) and immunohistochemistry. Immunohistochemical staining performed included α-SMA (DakoCytomation, Carpinteria, Calif.) for detecting activation of HSCs and Sirius red staining for detecting collagen deposition. Stained liver tissues were imaged under light microscopy (Olympus America) and α-SMA or Sirius red positive area was quantified in 20 fields of each sample using ImageJ software (NIH). For detection of apoptosis, TUNEL-Fluorescein (R&D systems, Gaithersburg, Md.) was used according to the manufacturer's instruction on liver sections as described above.

Results

Figure 3:
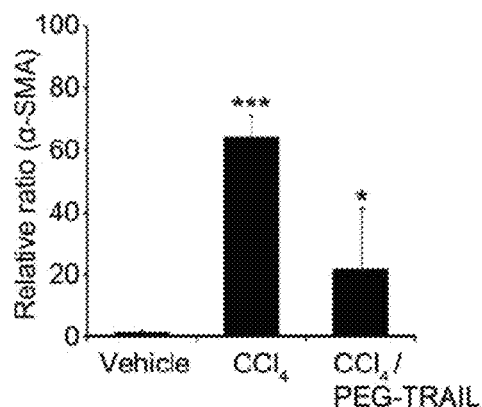
FIG. 3 is bar graphs showing relative protein expression levels of alpha-SMA (α-SMA), a marker of stellate cell activation, in western blots from isolated liver tissues treated with vehicle, CCl4 alone and CCl4 with PEG-TRAIL. α-SMA levels were significantly increased when rats were treated with CCl4, however, PEG-TRAIL reduced the expression of α-SMA. ***P<0.001 vs. vehicle, *P<0.05 vs. CCl4.
Figure 4A:
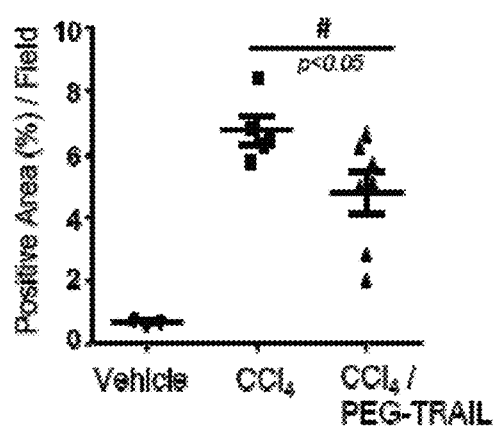
FIGS. 4A and 4B are dot plots of quantified collagen deposition (Sirius red stain, FIG. 4A) and α-SMA positive area (FIG. 4B) in 20 fields of each liver sample.
Figure 4B:
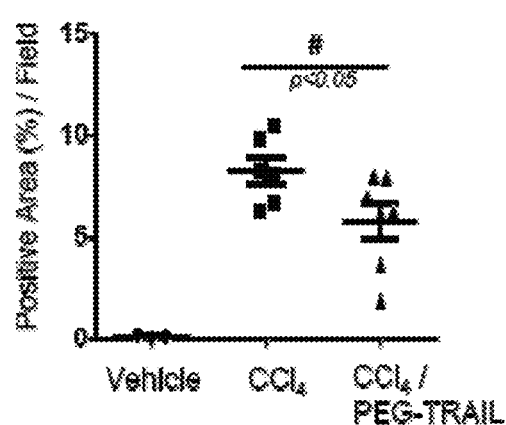

Western blot analysis showed that TRAIL-R (TRAIL receptor in rats) was up-regulated in both CCl4 treated and CCl4 combined with PEG-TRAIL treated groups however, expression of fibrotic markers, PAI-1 and alpha-SMA (α-SMA), were significantly reduced in the PEG-TRAIL group compared to that of CCl4 and control groups (FIG. 3). Immunohistochemical analyses of alpha-SMA and Sirius red demonstrated that rats treated with PEG-TRAIL showed significant reduction in fibrosis compared to CCl4-treated rats without PEG-TRAIL ($p<0.05$). Analyzed images were quantified as positive area (%) per field (FIGS. 4A and 4B). To validate if reduced alpha-SMA (α-SMA) and collagen is due to the TRAIL-induced apoptosis in activated HSCs, liver tissues were analyzed by TUNEL assay. TUNEL positive cells were strongly detected only in CCl4 and PEG-TRAIL combined group but were not detected in other control groups, olive oil, saline and CCl4 treated groups. qPCR of mRNA obtained from liver tissues treated with PEG-TRAIL revealed an obvious reduction of multiple, highly upregulated fibrosis-related genes associated with the activated HSCs including TRAIL-R, α-SMA, collagen 1, collagen 3, TGF-β1, MMP-2, MMP-3, PDGFR, TIMP-1, TIMP-3 and BMP-7 ($p<0.05$ vs. non-PEG-TRAIL-treated CCl4 group). Western blot analyses confirmed declined expression levels of these genes at the protein levels in the PEG-TRAIL treated group.

In addition, hydroxyproline levels were lower in PEG-TRAIL-treated group over the non-treated group, and these results were consistent with lower levels of liver weight-body weight (LW/BW) ratio, alkaline phosphatase and total bilirubin ($p<0.05$ vs. non-PEG-TRAIL-treated CCl4 group). Overall, these in vivo results clearly demonstrate that liver fibrogenesis can be reversed and/or inhibited by eliminating activated HSCs and simultaneously reducing multiple fibrosis-associated molecules by treating fibrotic livers with TRAIL and its agonists.

Example 5: The Treatment with PEGylated TRAIL Ameliorates Liver Cirrhosis and Reduces Ascites Incidence and Volume Materials and Methods Liver Cirrhosis Induced by CC4 in Rats (Group 3)

6-8 week old SD rats (Hanlim Experimental Animal Laboratory) were divided for 3 groups (8-10 rats per group); i) vehicle (olive oil), ii) 20% CCl4 in olive oil and iii) CCl4 in olive oil and PEG-TRAIL. Rats were firstly administered with CCl4 (2 ml/kg) three times per week via intraperitoneal injection or olive oil as control groups for 8 weeks. At the 8 week timepoint, rats were treated with 4 mg/kg of intravenously administered PEG-TRAIL every other day for 2 weeks or treated with the same amount of saline for control groups, along with continuing CCl4 or olive oil treatment (Group 3, FIG. 2).

Western Blot Analyses and qPCR

Regulation patterns of TRAIL-R, α-SMA and fibrosis-associated molecules listed above in isolated liver tissues at protein and mRNA levels were analyzed by western blotting and qPCR as described above.

Liver Histology and Immunohistochemistry of Liver Fibrosis

Liver tissues were fixed in 10% buffered formalin, embedded in paraffin, and cut into 4 μm thick sections. The sections were then stained with hematoxylin and eosin (H&E) and immunohistochemistry. Immunohistochemical staining included α-SMA (DakoCytomation, Carpinteria, Calif.) for detecting activation of HSCs and Sirius red staining for detecting collagen deposition. Stained liver tissues were imaged under light microscopy (Olympus America) and α-SMA or Sirius red positive areas were quantified in fields of each sample using ImageJ software (NIH).

Collection and Measurement of Ascitic Fluid

When ascites occurred during the treatment, rats were euthanized and ascitic fluid was collected by a sterilized syringe from the peritoneum of rats. Volume, cell count, total protein and albumin concentrations of the ascitic fluid was measured to determine the serum-ascites albumin gradient (SAAG) which has been proven in prospective studies to categorize ascites.

Results

Figure 5:
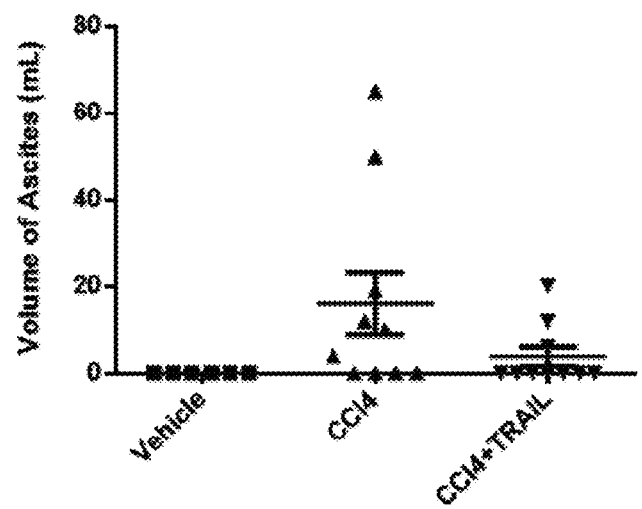
FIG. 5 is a dot plot of the volume of ascites (ml) in mice from Group 3 (FIG. 2) treated with vehicle, CCl4+vehicle, and CCl4+PEG-TRAIL.

After 10 week of CCl4 treatment alone, all rats showed micronodular liver cirrhosis with discrete signs of inflammation. Ascites was found in six rats with a volume ranging from 4-65 ml. Isolated livers showed clear morphological damages. Strong signs of collagen deposition were found from the liver tissues via Sirus red staining as compared to rats treated with CCl4 for only 6 weeks. In contrast, rats treated with CCl4 and PEG-TRAIL showed morphologically normal livers compared to that of rats treated with CCl4 alone. In addition, PEG-TRAIL treated liver tissues clearly showed a tendency of lower fibrotic markers, namely α-SMA and collagen, as revealed by immunohistochemistry. In addition, PEG-TRAIL treatment increased serum levels of total protein and albumin while significantly lowering bilirubin and hydroxproline levels in the liver tissues compared to CCl4-treated rats with PEG-TRAIL ($p<0.05$ vs. non-PEG-TRAIL-treated CCl4 group). As demonstrated in liver fibrosis models, PEG-TRAIL treatment substantially down-regulated molecules associated with fibrogenesis at the protein and mRNA levels. Relative fold-changes from the PEG-TRAIL-treated group in multiple expressions, including TRAIL-R, α-SMA, collagen 1, collagen 3, TGF-β1, MMP-2, MMP-3, PDGFR, TIMP-1, TIMP-3 were significantly lower than that of non-PEG-TRAIL-treated CCl4 groups ($p<0.05$ vs. non-PEG-TRAIL-treated group). Ascites is one of the major complications in cirrhosis. 60% (6 out of 10) of rats treated with CCl4 for 8-10 weeks developed ascites. In contrast, rats treated with CCl4 with PEG-TRAIL demonstrated reduced incidence rate of ascites of only 30% (3 out of 10). In particular, the volume of ascitic fluid was significantly reduced in the PEGTRAIL treated group compared to the CCl4 without PEG-TRAIL group (FIG. 5). Taken together, treatment of PEG-TRAIL reverses and inhibits the progression of cirrhosis while reducing ascites incidence in rats with cirrhotic liver diseases.

Example 6: The Treatment of PEGylated TRAIL Reverses Pancreatic Fibrosis in Alcohol-Induced Chronic Pancreatitis Rat Models Materials and Methods Chronic Pancreatitis (CP) Induced by Ethanol/Cerulein/LD Liquid Diet in Rats SD rats at 6-8 weeks old (Hanlim Experimental Animal Laboratory) were divided into 3 groups (8-10 rats per group); i) vehicle (PBS), ii) CP rats treated with vehicle iii) CP rats treated with TRAIL. A model of experimental alcohol-induced CP was induced in rats as reported elsewhere (Deng, X., et at., Am. J. Pathol. 166(1):93-106 (2005)). 3 groups of rats were fed a LD liquid diet with gradually increased ethanol concentrations from 0 to 36% for seven days and then fed 36% ethanol for three weeks. Rats were intraperitoneally injected with 20 microgram/kg (μg/kg) of cerulein (Sigma) for four hourly injections once a week until day 28. The rats were intravenously treated with PEG-TRAIL (4 mg/kg) or PBS daily for six days from day 23 to 28. Control group was treated with PBS. After treatments, pancreas specimens were analyzed by immunohistochemistry and western blotting. Pancreatic tissues were stained with H&E and Massons's trichrome stain (collagen) and analyzed for regulation of biomarkers including α-SMA, PDGFRβ, cleaved caspase-8, COX-2.

Results

Figure 6:
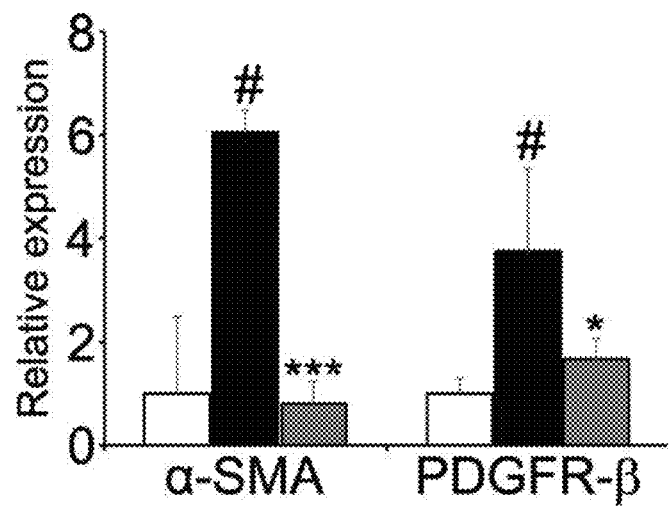
FIG. 6 is a bar graph showing relative protein expression levels of α-SMA, a marker of stellate cell activation, PDGFRβ, a marker of fibrosis, in western blots from isolated pancreatic tissues from healthy rats (white bars) and alcohol-induced chronic pancreatitis (CP) rats treated with ethanol/cerulein/Lieber Decarli (LD) diet (black bars) and ethanol/cerulein/LD with PEG-TRAIL (gray bars). α-SMA and PDGFRβ levels were significantly increased when rats were treated with ethanol/cerulein/LD, however, PEG-TRAIL reduced the expression of α-SMA and PDGFRβ. #P<0.05 vs. vehicle, ***P<0.001 vs. CP+vehicle, *P<0.05 vs. CP+vehicle.

In CP models, pancreatic fibrogenesis was clearly observed by H&E staining and highly expressed collagen. In addition, α-SMA (activated PSC marker) and fibrogenic markers such as PDGFRP were highly upregulated (6-fold and 4-fold vs. vehicle, respectively, $p<0.05$) (FIG. 6). PEG-TRAIL treatment significantly reduced collagen depositions, down-regulated α-SMA and PDGFβ (1-fold and 2-fold vs. vehicle, respectively) as well as other inflammatory markers including COX-2 as evidenced by western blot analysis ($p<0.05$ vs. non-PEG-TRAIL-treated CP group). Cleaved caspase-8 was significantly upregulated (13-fold vs. vehicle, $p<0.05$) only in PEG-TRAIL-treated CP, indicating that eradication of activated PSCs is due to TRAIL-mediated apoptosis.

I claim:

1. A method for reversing tissue fibrosis in a subject comprising administering by injection to the subject an effective amount of a pro-apoptotic TNF-related apoptosis-inducing ligand (TRAIL)-R1/DR4 or TRAIL-R2/DR5 receptor agonist selected from the group consisting of full length TRAIL comprising amino acids 1 to 281 of SEQ ID NO:1, full length TRAIL comprising amino acids 1 to 281 of SEQ ID NO:1 pegylated at the N-terminus, TRAIL functional fragments comprising at least amino acids 114-281 of SEQ ID NO:1, and TRAIL functional fragments comprising at least amino acids 114-281 of SEQ ID NO:1 pegylated at the N-terminus to induce apoptosis in hepatic stellate cells, pancreatic stellate cells, and activated myofibroblasts that produce or induce an excess amount of extracellular matrix resulting in fibrosis of an organ or tissue or cirrhosis.

2. The method of claim 1, wherein the fibrosis is cirrhosis of the liver.

3. The method of claim 1, wherein the fibrosis is fibrosis of the pancreas.

4. The method of claim 1, wherein the fibrosis is fibrosis of the lungs.

5. The method of claim 1 wherein the fibrosis is fibrosis of the skin.

6. The method of claim 1 wherein the pro-apoptotic TRAIL-R1/DR4 or TRAIL-R2/DR5 receptor agonist incorporated into or encapsulated by nanoparticles, microparticles, micelles, or liposomes.

7. The method of claim 6 wherein the pro-apoptotic TRAIL-R1/DR4 or TRAIL-R2/DR5 receptor agonist is formulated for delayed, sustained, or modified release.

8. The method of claim 1, wherein the pro-apoptotic TRAIL-R1/DR4 or TRAIL-R2/DR5 receptor agonist is TRAIL.

9. The method of claim 1, wherein the TRAIL receptor ligand comprises PEGylated TRAIL comprising a trimeric TRAIL comprising zipper amino acid motifs favoring trimer formation at the N-terminals thereof; and a polyethylene glycol (PEG) or a derivative thereof, wherein the PEG is bound to the N-terminal of at least one monomer of the trimeric TRAIL.

10. The method of claim 1, wherein the PEG or the derivative thereof has a linear or branched, trimeric form.

11. The method of claim 1, wherein the PEG or the derivative thereof is selected from the group consisting of methoxypolyethylene glycol succinimidyl propionate, methoxypolyethylene glycol N-hydroxysuccinimide, methoxypolyethylene glycol aldehyde, methoxypolyethylene glycol maleimide and multiple-branched polyethylene glycol.

12. The method of claim 11, wherein the PEG or the derivative thereof is methoxypolyethylene glycol aldehyde.

13. The method of claim 1, wherein the PEG or the derivative thereof has a molecular weight between 1,000 and 100,000.

14. The method of claim 13, wherein the PEG or the derivative thereof has a molecular weight between 5,000 and 50,000.

15. The method of claim 1 wherein the effective amount is administered prior to surgery, or at the time of or immediately after surgery.

16. The method of claim 1 wherein the effective amount is administered into and/or adjacent to a site of fibrosis or scarring in the liver, a site of excess extracellular matrix accumulation, a site of activated or proliferating hepatic stellate cells (HSC), or a site of another biochemical, histological, or morphological marker of diseased liver.

17. The method of claim 1 wherein an effective amount of the TRAIL receptor agonist is administered in two or more dosages.

18. The method of claim 1 wherein an effective amount of the TRAIL receptor agonist is released from a pharmaceutical formulation over a period of one or more days.

19. The method of claim 1 further comprising administering active agents in addition to the TRAIL-R1/DR4 or TRAIL-R2/DR5 receptor agonist.

20. The method of claim 1, wherein the consequence of unwanted scarring of an organ or tissue, cirrhosis, is ascites or pain.

\* \* \* \* \*

UNITED STATES PATENT AND TRADEMARK OFFICE
CERTIFICATE OF CORRECTION

PATENT NO. : 9,901,620 B2
APPLICATION NO. : 14/690142
DATED : February 27, 2018
INVENTOR(S) : Kang Choon Lee It is certified that error appears in the above-identified patent and that said Letters Patent is hereby corrected as shown below:

In the Specification

Column 1, Line 50, replace "Omary. M.B.," with --Omary, M.B.,--.
Column 1, Line 53, replace "a-smooth muscle actin" with --α-smooth muscle actin--.
Column 1, Line 63, replace "New Eng, J. Med.e," with --New Eng. J. Med.,--.
Column 2, Line 8, replace "PPAR-r" with --PPAR-γ--.
Column 2, Line 9, replace "PPAR-r" with --PPAR-γ--.
Column 2, Line 10, replace "PPAR-r" with --PPAR-γ--.
Column 2, Line 26, replace "ATIR" with --AT1R--.
Column 2, Line 38, replace "using TFG-β" with --using TGF-β--.
Column 2, Line 52, replace "undeserved" with --underserved--.
Column 4, Lines 51 and 52, replace "PEG-TRIAL" with --PEG-TRAIL--.
Column 4, Line 63, replace "if PEG-TRAIL prevents" with --if TRAIL prevents--.
Column 5, Line 1, replace "FIG. 3 is bar graphs" with --FIG. 3 is a bar graph--.
Column 6, Line 35, replace "polypeptides of in disclosure" with --polypeptides of the disclosure--.
Column 7, Line 32, replace "(Lys: Arg). (Met:" with --(Lys: Arg), (Met:--.
Column 7, Line 35, replace "60%. 70%," with --60%, 70%,--.
Column 7, Line 46, replace "described in (Computational" with --described in Computational--.
Column 8, Line 2, replace "that is be 100%" with --that is 100%--.
Column 8, Lines 46 and 47, replace "Pancreatic Disease Ligands" with --Pancreatic Disease and Ligands--.
Column 8, Line 63, replace "mimic, or mimic" with --or mimic--.
Column 9, Line 14, replace "TIMP-3, BMP-7" with --TIMP-3, and BMP-7--.
Column 9, Line 16, replace "in amount effective" with --in an amount effective--.
Column 10, Line 2, replace "95-281, and 114-281" with --95-281, or 114-281--.
Column 10, Line 23, replace "function fragment" with --functional fragment--.
Column 10, Lines 52 and 53, replace "In a particular embodiments" with --In particular embodiments--.
Column 10, Line 59, replace "D269H/E 95R" with --D269H/E195R--.

Signed and Sealed this
Ninth Day of April, 2019

Andrei Iancu
*Director of the United States Patent and Trademark Office*

CERTIFICATE OF CORRECTION (continued)

Column 15, Lines 11 and 12, replace "the desired antagonistic activity" with --the desired activity--.
Column 16, Line 4, replace "constant region (Fe)," with --constant region (Fc),--.
Column 17, Line 35, replace "The antibodies can be a hybrid antibody." with --The antibodies can be hybrid antibodies.--.
Column 19, Lines 2 and 3, replace "Fee, et al., Biotechnol Bioeng., 98(4):725-3 (2007)" with --(Fee, et al., Biotechnol Bioeng., 98(4):725-3 (2007))--.
Column 20, Line 32, replace "proteins such as hyaluronic acid" with --hyaluronic acid--.
Column 20, Line 34, replace "cellulose, polyvinyl alcohol" with --cellulose,--.
Column 20, Line 38, replace "such as found" with --such as those found--.
Column 20, Line 40, replace "amines. (Molineux" with --amines (Molineux--.
Column 20, Line 42, replace "such as found" with --such as those found--.
Column 20, Line 58, replace "include acylic" with --include acrylic--.
Column 21, Line 12, replace "8729 (2011)" with --8729 (2011))--.
Column 21, Line 21, replace "time released" with --timed release--.
Column 21, Line 23, replace "time released" with --timed release--.
Column 22, Line 31, replace "HAS) which recognizes" with --HAS), which recognizes--.
Column 23, Line 40, replace "after coupled to the pro-apoptotic agents" with --after coupling to the pro-apoptotic agents--.
Column 26, Line 63, replace "or scarring are disclosed." with --or scarring.--.
Column 27, Line 6, replace "ofa pro-poptotic" with --of a pro-apoptotic--.
Column 27, Line 54, replace "preisinusoidal cells" with --perisinusoidal cells--.
Column 28, Line 44, replace "embodiment the target cells" with --embodiment, the target cells--.
Column 28, Line 52, replace "in effective amount" with --in an effective amount--.
Column 29, Line 37, replace "particular useful" with --particularly useful--.
Column 30, Line 23, replace "sensitive of cells" with --sensitivity of cells--.
Column 30, Lines 46 and 47, replace "phosphatidylcholine (PPC)" with --phosphatidylcholine (PC)--.
Column 31, Line 7, replace "thereof.An exemplary" with --thereof. An exemplary--.
Column 31, Line 18, replace "(2009)." with --(2009)).--.
Column 31, Lines 20 and 21, replace "and (Glassner," with --and Glassner,--.
Column 31, Line 33, replace "Thi responses." with --Th1 responses.--.
Column 31, Line 50, replace "TGF-b expression" with --TGF-β expression--.
Column 32, Line 8, replace "is more effective the sum" with --is more effective than the sum--.
Column 32, Line 17, replace "doxorubicin,5-fluorouracil" with --doxorubicin, 5-fluorouracil--.
Column 33, Line 2, replace "after to the first administration" with --after the first administration--.
Column 34, Line 62, replace "MatTek corporation" with --MatTek Corporation--.
Column 36, Line 30, replace "into 4 m thick" with --into 4 μm thick--.
Column 36, Line 31, replace "hematoxylin and cosin" with --hematoxylin and eosin--.
Column 36, Line 51, replace "Dakocytomation" with --DakoCytomation--.
Column 37, Line 30, replace "rat were" with --rats were--.
Column 38, Line 19, replace "collage" with --collagen--.
Column 38, Line 31, replace "into 4 m thick" with --into 4 μm thick--.
Column 39, Line 20, replace "CC4 in Rats" with --CCl4 in Rats--.
Column 39, Line 22, replace "divided for 3 groups" with --divided into 3 groups--.
Column 39, Line 63, replace "Sirus" with --Sirius--.
Column 40, Line 5, replace "hydroxproline" with --hydroxyproline--.
Column 40, Line 21, replace "PEGTRAIL" with --PEG-TRAIL--.

CERTIFICATE OF CORRECTION (continued)
U.S. Pat. No. 9,901,620 B2

Column 40, Line 57, replace "PDGFRP" with --PDGFRβ--.
Column 40, Line 60, replace "and PDGFβ" with --and PDGFRβ--.

In the Claims

Claim 6, Column 43, Line 59, replace "agonist incorporated" with --agonist is incorporated--.
Claim 20, Column 45, Line 10, replace "wherein the consequence" with --wherein consequence--.
Claim 20, Column 45, Line 11, replace "tissue, cirrhosis, is" with --tissue or cirrhosis is--.